(12) United States Patent
Hayter et al.

(10) Patent No.: US 11,553,883 B2
(45) Date of Patent: Jan. 17, 2023

(54) SYSTEM, DEVICE AND METHOD OF DYNAMIC GLUCOSE PROFILE RESPONSE TO PHYSIOLOGICAL PARAMETERS

(71) Applicant: Abbott Diabetes Care Inc., Alameda, CA (US)

(72) Inventors: Gary Alan Hayter, Oakland, CA (US); Nathan Christopher Crouther, San Francisco, CA (US); Michael Love, Pleasanton, CA (US); Erwin Satrya Budiman, Fremont, CA (US); Daniel Milfred Bernstein, El Granada, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 1176 days.

(21) Appl. No.: 15/742,502

(22) PCT Filed: Jul. 8, 2016

(86) PCT No.: PCT/US2016/041632
§ 371 (c)(1),
(2) Date: Jan. 6, 2018

(87) PCT Pub. No.: WO2017/011346
PCT Pub. Date: Jan. 19, 2017

(65) Prior Publication Data
US 2018/0199890 A1      Jul. 19, 2018

Related U.S. Application Data

(60) Provisional application No. 62/307,346, filed on Mar. 11, 2016, provisional application No. 62/191,218, filed on Jul. 10, 2015.

(51) Int. Cl.
*A61B 5/145* (2006.01)
*A61B 5/00* (2006.01)
(Continued)

(52) U.S. Cl.
CPC .......... *A61B 5/7246* (2013.01); *A61B 5/0022* (2013.01); *A61B 5/1118* (2013.01);
(Continued)

(58) Field of Classification Search
CPC .. A61B 5/7246; A61B 5/1118; A61B 5/14532
See application file for complete search history.

(56) References Cited

U.S. PATENT DOCUMENTS 3,581,062 A    5/1971   Aston
3,926,760 A    12/1975  Allen et al.
(Continued)

FOREIGN PATENT DOCUMENTS

EP    0098592    1/1984
EP    0127958    12/1984
(Continued)

OTHER PUBLICATIONS

Metcalf et al. "Effects of Moderate-to-Vigorous Intensity Physical Activity on Overnight and Next-Day Hypoglycemia in Active Adolescents With Type 1 Diabetes." 2014;37(5):1272-8. doi: 10.2337/dc13-1973. (Year: 2014).*

(Continued)

*Primary Examiner* — Meredith Weare
(74) *Attorney, Agent, or Firm* — Baker Botts L.L.P.

(57) ABSTRACT

Method, device and system for providing consistent and reliable glucose response information to physiological changes and/or activities is provided to improve glycemic control and health management.

70 Claims, 15 Drawing Sheets

(51) Int. Cl.
  *A61B 5/11* (2006.01)
  *G16B 40/10* (2019.01)
  *G16H 40/63* (2018.01)
  *A61B 5/024* (2006.01)
  *A61B 5/1486* (2006.01)

(52) U.S. Cl.
  CPC ........ *A61B 5/1451* (2013.01); *A61B 5/14532* (2013.01); *A61B 5/4839* (2013.01); *A61B 5/4866* (2013.01); *A61B 5/7275* (2013.01); *G16B 40/10* (2019.02); *G16H 40/63* (2018.01); *A61B 5/024* (2013.01); *A61B 5/1114* (2013.01); *A61B 5/1123* (2013.01); *A61B 5/1486* (2013.01); *A61B 2560/0223* (2013.01)

(56) References Cited

U.S. PATENT DOCUMENTS

| | | |
|---|---|---|
| 3,949,388 A | 4/1976 | Fuller |
| 3,960,497 A | 6/1976 | Acord et al. |
| 4,033,330 A | 7/1977 | Willis et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,243,696 A | 9/1993 | Carr et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,552,997 A | 9/1996 | Massart |
| 5,555,190 A | 9/1996 | Derby et al. |
| 5,564,434 A | 10/1996 | Halperin et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,324 A | 5/1997 | Sarbach |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,726,646 A | 3/1998 | Bane et al. |
| 5,733,259 A | 3/1998 | Valcke et al. |
| 5,735,285 A | 4/1998 | Albert et al. |
| 5,748,103 A | 5/1998 | Flach et al. |
| 5,749,907 A | 5/1998 | Mann |
| 5,772,586 A | 6/1998 | Heinonen et al. |
| 5,791,344 A | 8/1998 | Schulman et al. |
| 5,804,047 A | 9/1998 | Kambe et al. |
| 5,833,603 A | 11/1998 | Kovacs et al. |
| 5,842,189 A | 11/1998 | Keeler et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,919,141 A | 7/1999 | Money et al. |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |

(56) References Cited

U.S. PATENT DOCUMENTS

| | | |
|---|---|---|
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmarm |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,143,164 A | 11/2000 | Heller et al. |
| 6,144,871 A | 11/2000 | Saito et al. |
| 6,157,850 A | 12/2000 | Diab et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,347 B1 | 10/2001 | Pompei |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,514,718 B2 | 2/2003 | Heller et al. |
| 6,520,326 B2 | 2/2003 | McIvor et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,025 B1 | 5/2004 | Platt |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |

(56) References Cited

U.S. PATENT DOCUMENTS

| | | |
|---|---|---|
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,011,630 B2 | 3/2006 | Desai et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,046,153 B2 | 5/2006 | Oja et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Pudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,711,493 B2 | 5/2010 | Bartkowiak et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,741,734 B2 | 6/2010 | Joannopoulos et al. |
| 7,751,864 B2 | 7/2010 | Buck, Jr. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,778,680 B2 | 8/2010 | Goode et al. |
| 7,779,332 B2 | 8/2010 | Karr et al. |
| 7,782,192 B2 | 8/2010 | Jeckelmann et al. |
| 7,783,333 B2 | 8/2010 | Brister et al. |

(56) References Cited

U.S. PATENT DOCUMENTS

| | | |
|---|---|---|
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,831,310 B2 | 11/2010 | Lebel et al. |
| 7,857,760 B2 | 12/2010 | Brister et al. |
| 7,860,574 B2 | 12/2010 | Von Arx et al. |
| 7,882,611 B2 | 2/2011 | Shah et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,984 B2 | 5/2011 | Brister et al. |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,996,158 B2 | 8/2011 | Hayter et al. |
| 7,999,674 B2 | 8/2011 | Kamen |
| 8,005,524 B2 | 8/2011 | Brauker et al. |
| 8,010,174 B2 | 8/2011 | Goode et al. |
| 8,010,256 B2 | 8/2011 | Oowada |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,900 B2 | 4/2012 | Taub et al. |
| 8,170,803 B2 | 5/2012 | Kamath et al. |
| 8,179,266 B2 | 5/2012 | Hermle |
| 8,192,394 B2 | 6/2012 | Estes et al. |
| 8,216,138 B1 | 7/2012 | McGarraugh et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,282,549 B2 | 10/2012 | Brauker et al. |
| 8,374,668 B1 | 2/2013 | Hayter et al. |
| 8,376,945 B2 | 2/2013 | Hayter et al. |
| 8,377,271 B2 | 2/2013 | Mao et al. |
| 8,409,093 B2 | 4/2013 | Bugler |
| 8,444,560 B2 | 5/2013 | Hayter et al. |
| 8,461,985 B2 | 6/2013 | Fennell et al. |
| 8,478,557 B2 | 7/2013 | Hayter et al. |
| 8,484,005 B2 | 7/2013 | Hayter et al. |
| 8,543,354 B2 | 9/2013 | Luo et al. |
| 8,560,038 B2 | 10/2013 | Hayter et al. |
| 8,571,808 B2 | 10/2013 | Hayter |
| 8,583,205 B2 | 11/2013 | Budiman et al. |
| 8,597,570 B2 | 12/2013 | Terashima et al. |
| 8,600,681 B2 | 12/2013 | Hayter et al. |
| 8,612,163 B2 | 12/2013 | Hayter et al. |
| 8,657,746 B2 | 2/2014 | Roy |
| 8,682,615 B2 | 3/2014 | Hayter et al. |
| 8,710,993 B2 | 4/2014 | Hayter et al. |
| 8,834,366 B2 | 9/2014 | Hayter et al. |
| 8,845,536 B2 | 9/2014 | Brauker et al. |
| 9,060,719 B2 | 6/2015 | Hayter et al. |
| 9,289,179 B2 | 3/2016 | Hayter et al. |
| 9,398,872 B2 | 7/2016 | Hayter et al. |
| 9,408,566 B2 | 8/2016 | Hayter et al. |
| 9,439,586 B2 | 9/2016 | Bugler |
| 9,483,608 B2 | 11/2016 | Hayter et al. |
| 9,558,325 B2 | 1/2017 | Hayter et al. |
| 9,743,872 B2 | 8/2017 | Hayter et al. |
| 2001/0037366 A1 | 11/2001 | Webb et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0065454 A1 | 5/2002 | Lebel et al. |
| 2002/0068860 A1 | 6/2002 | Clark |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0150959 A1 | 10/2002 | Lejeunne et al. |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |

(56) References Cited

U.S. PATENT DOCUMENTS

| | | | |
|---|---|---|---|
| 2003/0208113 A1* | 11/2003 | Mault | A61B 5/14532 |
| | | | 600/316 |
| 2003/0212317 A1 | 11/2003 | Kovatchev et al. | |
| 2003/0212379 A1 | 11/2003 | Bylund et al. | |
| 2003/0216630 A1 | 11/2003 | Jersey-Willuhn et al. | |
| 2003/0217966 A1 | 11/2003 | Tapsak et al. | |
| 2003/0235817 A1 | 12/2003 | Bartkowiak et al. | |
| 2004/0010186 A1 | 1/2004 | Kimball et al. | |
| 2004/0010207 A1 | 1/2004 | Flaherty et al. | |
| 2004/0011671 A1 | 1/2004 | Shults et al. | |
| 2004/0024553 A1 | 2/2004 | Monfre et al. | |
| 2004/0034289 A1 | 2/2004 | Teller et al. | |
| 2004/0039298 A1 | 2/2004 | Abreu | |
| 2004/0040840 A1 | 3/2004 | Mao et al. | |
| 2004/0041749 A1 | 3/2004 | Dixon | |
| 2004/0045879 A1 | 3/2004 | Shults et al. | |
| 2004/0054263 A1 | 3/2004 | Moerman et al. | |
| 2004/0063435 A1 | 4/2004 | Sakamoto et al. | |
| 2004/0064068 A1 | 4/2004 | DeNuzzio et al. | |
| 2004/0099529 A1 | 5/2004 | Mao et al. | |
| 2004/0106858 A1 | 6/2004 | Say et al. | |
| 2004/0111017 A1 | 6/2004 | Say et al. | |
| 2004/0117204 A1 | 6/2004 | Mazar et al. | |
| 2004/0122353 A1 | 6/2004 | Shahmirian et al. | |
| 2004/0133164 A1 | 7/2004 | Funderburk et al. | |
| 2004/0133390 A1 | 7/2004 | Osorio et al. | |
| 2004/0135571 A1 | 7/2004 | Uutela et al. | |
| 2004/0135684 A1 | 7/2004 | Steinthal et al. | |
| 2004/0138588 A1 | 7/2004 | Saikley et al. | |
| 2004/0142403 A1 | 7/2004 | Hetzel et al. | |
| 2004/0146909 A1 | 7/2004 | Duong et al. | |
| 2004/0147872 A1 | 7/2004 | Thompson | |
| 2004/0152622 A1 | 8/2004 | Keith et al. | |
| 2004/0162678 A1 | 8/2004 | Hetzel et al. | |
| 2004/0167464 A1 | 8/2004 | Ireland et al. | |
| 2004/0167801 A1 | 8/2004 | Say et al. | |
| 2004/0171921 A1 | 9/2004 | Say et al. | |
| 2004/0176672 A1 | 9/2004 | Silver et al. | |
| 2004/0186362 A1 | 9/2004 | Brauker et al. | |
| 2004/0186365 A1 | 9/2004 | Jin et al. | |
| 2004/0193020 A1 | 9/2004 | Chiba et al. | |
| 2004/0193025 A1 | 9/2004 | Steil et al. | |
| 2004/0193090 A1 | 9/2004 | Lebel et al. | |
| 2004/0197846 A1 | 10/2004 | Hockersmith et al. | |
| 2004/0199056 A1 | 10/2004 | Husemann et al. | |
| 2004/0199059 A1 | 10/2004 | Brauker et al. | |
| 2004/0204687 A1 | 10/2004 | Mogensen et al. | |
| 2004/0204868 A1 | 10/2004 | Maynard et al. | |
| 2004/0219664 A1 | 11/2004 | Heller et al. | |
| 2004/0225338 A1 | 11/2004 | Lebel et al. | |
| 2004/0236200 A1 | 11/2004 | Say et al. | |
| 2004/0249253 A1 | 12/2004 | Racchini et al. | |
| 2004/0254433 A1 | 12/2004 | Bandis et al. | |
| 2004/0254434 A1 | 12/2004 | Goodnow et al. | |
| 2004/0260478 A1 | 12/2004 | Schwamm | |
| 2004/0267300 A1 | 12/2004 | Mace | |
| 2005/0001024 A1 | 1/2005 | Kusaka et al. | |
| 2005/0004439 A1 | 1/2005 | Shin et al. | |
| 2005/0004494 A1 | 1/2005 | Perez et al. | |
| 2005/0010269 A1 | 1/2005 | Lebel et al. | |
| 2005/0017864 A1 | 1/2005 | Tsoukalis | |
| 2005/0027177 A1 | 2/2005 | Shin et al. | |
| 2005/0027180 A1 | 2/2005 | Goode et al. | |
| 2005/0027181 A1 | 2/2005 | Goode et al. | |
| 2005/0027182 A1 | 2/2005 | Siddiqui et al. | |
| 2005/0027462 A1 | 2/2005 | Goode et al. | |
| 2005/0027463 A1 | 2/2005 | Goode et al. | |
| 2005/0031689 A1 | 2/2005 | Shults et al. | |
| 2005/0038332 A1 | 2/2005 | Saidara et al. | |
| 2005/0043598 A1 | 2/2005 | Goode et al. | |
| 2005/0049179 A1 | 3/2005 | Davidson et al. | |
| 2005/0049473 A1 | 3/2005 | Desai et al. | |
| 2005/0070774 A1 | 3/2005 | Addison et al. | |
| 2005/0070777 A1 | 3/2005 | Cho et al. | |
| 2005/0090607 A1 | 4/2005 | Tapsak et al. | |
| 2005/0096511 A1 | 5/2005 | Fox et al. | |
| 2005/0096512 A1 | 5/2005 | Fox et al. | |
| 2005/0096516 A1 | 5/2005 | Soykan et al. | |
| 2005/0112169 A1 | 5/2005 | Brauker et al. | |
| 2005/0113648 A1 | 5/2005 | Yang et al. | |
| 2005/0113653 A1 | 5/2005 | Fox et al. | |
| 2005/0113886 A1 | 5/2005 | Fischell et al. | |
| 2005/0114068 A1 | 5/2005 | Chey et al. | |
| 2005/0115832 A1 | 6/2005 | Simpson et al. | |
| 2005/0116683 A1 | 6/2005 | Cheng et al. | |
| 2005/0121322 A1 | 6/2005 | Say et al. | |
| 2005/0131346 A1 | 6/2005 | Douglas | |
| 2005/0134731 A1 | 6/2005 | Lee et al. | |
| 2005/0137530 A1 | 6/2005 | Campbell et al. | |
| 2005/0143635 A1 | 6/2005 | Kamath et al. | |
| 2005/0154271 A1 | 7/2005 | Rasdal et al. | |
| 2005/0176136 A1 | 8/2005 | Burd et al. | |
| 2005/0177398 A1 | 8/2005 | Watanabe et al. | |
| 2005/0182306 A1 | 8/2005 | Sloan | |
| 2005/0187442 A1 | 8/2005 | Cho et al. | |
| 2005/0187720 A1 | 8/2005 | Goode, Jr. et al. | |
| 2005/0192494 A1 | 9/2005 | Ginsberg | |
| 2005/0192557 A1 | 9/2005 | Brauker et al. | |
| 2005/0195930 A1 | 9/2005 | Spital et al. | |
| 2005/0196821 A1 | 9/2005 | Monfre et al. | |
| 2005/0197793 A1 | 9/2005 | Baker, Jr. | |
| 2005/0199494 A1 | 9/2005 | Say et al. | |
| 2005/0203360 A1 | 9/2005 | Brauker et al. | |
| 2005/0204134 A1 | 9/2005 | Von Arx et al. | |
| 2005/0214892 A1 | 9/2005 | Kovatchev et al. | |
| 2005/0236361 A1 | 10/2005 | Ufer et al. | |
| 2005/0239154 A1 | 10/2005 | Feldman et al. | |
| 2005/0239156 A1 | 10/2005 | Drucker et al. | |
| 2005/0241957 A1 | 11/2005 | Mao et al. | |
| 2005/0245795 A1 | 11/2005 | Goode, Jr. et al. | |
| 2005/0245799 A1 | 11/2005 | Brauker et al. | |
| 2005/0245839 A1 | 11/2005 | Stivoric et al. | |
| 2005/0245904 A1 | 11/2005 | Estes et al. | |
| 2005/0251033 A1 | 11/2005 | Scarantino et al. | |
| 2005/0272985 A1 | 12/2005 | Kotulla et al. | |
| 2005/0277164 A1 | 12/2005 | Drucker et al. | |
| 2005/0277912 A1 | 12/2005 | John | |
| 2005/0287620 A1 | 12/2005 | Heller et al. | |
| 2006/0001538 A1 | 1/2006 | Kraft et al. | |
| 2006/0001551 A1 | 1/2006 | Kraft et al. | |
| 2006/0004270 A1 | 1/2006 | Bedard et al. | |
| 2006/0010098 A1 | 1/2006 | Goodnow et al. | |
| 2006/0015020 A1 | 1/2006 | Neale et al. | |
| 2006/0015024 A1 | 1/2006 | Brister et al. | |
| 2006/0016700 A1 | 1/2006 | Brister et al. | |
| 2006/0017923 A1 | 1/2006 | Ruchti et al. | |
| 2006/0019327 A1 | 1/2006 | Brister et al. | |
| 2006/0020186 A1 | 1/2006 | Brister et al. | |
| 2006/0020187 A1 | 1/2006 | Brister et al. | |
| 2006/0020188 A1 | 1/2006 | Kamath et al. | |
| 2006/0020189 A1 | 1/2006 | Brister et al. | |
| 2006/0020190 A1 | 1/2006 | Kamath et al. | |
| 2006/0020191 A1 | 1/2006 | Brister et al. | |
| 2006/0020192 A1 | 1/2006 | Brister et al. | |
| 2006/0020300 A1 | 1/2006 | Nghiem et al. | |
| 2006/0025663 A1 | 2/2006 | Talbot et al. | |
| 2006/0029177 A1 | 2/2006 | Cranford, Jr. et al. | |
| 2006/0031094 A1 | 2/2006 | Cohen et al. | |
| 2006/0036139 A1 | 2/2006 | Brister et al. | |
| 2006/0036140 A1 | 2/2006 | Brister et al. | |
| 2006/0036141 A1 | 2/2006 | Kamath et al. | |
| 2006/0036142 A1 | 2/2006 | Brister et al. | |
| 2006/0036143 A1 | 2/2006 | Brister et al. | |
| 2006/0036144 A1 | 2/2006 | Brister et al. | |
| 2006/0036145 A1 | 2/2006 | Brister et al. | |
| 2006/0058588 A1 | 3/2006 | Zdeblick | |
| 2006/0079740 A1 | 4/2006 | Silver et al. | |
| 2006/0091006 A1 | 5/2006 | Wang et al. | |
| 2006/0142651 A1 | 6/2006 | Brister et al. | |
| 2006/0154642 A1 | 7/2006 | Scannell | |
| 2006/0155180 A1 | 7/2006 | Brister et al. | |
| 2006/0156796 A1 | 7/2006 | Burke et al. | |
| 2006/0166629 A1 | 7/2006 | Reggiardo | |
| 2006/0173260 A1 | 8/2006 | Gaoni et al. | |

(56) References Cited

U.S. PATENT DOCUMENTS

| | | |
|---|---|---|
| 2006/0173406 A1 | 8/2006 | Hayes et al. |
| 2006/0173444 A1 | 8/2006 | Choy et al. |
| 2006/0183984 A1 | 8/2006 | Dobbies et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbies et al. |
| 2007/0055799 A1 | 3/2007 | Koehler et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0151869 A1 | 7/2007 | Heller et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichom et al. |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021436 A1 | 1/2008 | Wolpert et al. |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |

(56) References Cited

U.S. PATENT DOCUMENTS

| | | |
|---|---|---|
| 2008/0208026 A1 | 8/2008 | Noujaim et al. |
| 2008/0208113 A1 | 8/2008 | Damiano et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub et al. |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariah et al. |
| 2009/0137887 A1 | 5/2009 | Shariah et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariah et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariah et al. |
| 2009/0192722 A1 | 7/2009 | Shariah et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0267765 A1 | 10/2009 | Greene et al. |
| 2009/0287073 A1 | 11/2009 | Boock et al. |
| 2009/0287074 A1 | 11/2009 | Shults et al. |

(56) References Cited

U.S. PATENT DOCUMENTS

| | | |
|---|---|---|
| 2009/0289796 A1 | 11/2009 | Blumberg |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0056992 A1 | 3/2010 | Hayter et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0064764 A1 | 3/2010 | Hayter et al. |
| 2010/0076283 A1 | 3/2010 | Simpson et al. |
| 2010/0081906 A1 | 4/2010 | Hayter et al. |
| 2010/0081908 A1 | 4/2010 | Dobbies et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094111 A1 | 4/2010 | Heller et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |
| 2010/0145262 A1 | 6/2010 | Bengtsson et al. |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213080 A1 | 8/2010 | Celentano et al. |
| 2010/0230285 A1 | 9/2010 | Hoss et al. |
| 2010/0234710 A1 | 9/2010 | Budiman et al. |
| 2010/0240975 A1 | 9/2010 | Goode et al. |
| 2010/0261987 A1 | 10/2010 | Kamath et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0292948 A1 * | 11/2010 | Feldman .............. A61B 5/0004 702/104 |
| 2010/0312176 A1 | 12/2010 | Lauer et al. |
| 2010/0313105 A1 | 12/2010 | Nekoomaram et al. |
| 2011/0004085 A1 | 1/2011 | Mensinger et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0053121 A1 * | 3/2011 | Heaton .............. A61B 5/14532 434/127 |
| 2011/0054282 A1 | 3/2011 | Nekoomaram et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0112696 A1 | 5/2011 | Yodfat et al. |
| 2011/0148905 A1 | 6/2011 | Simmons et al. |
| 2011/0152637 A1 | 6/2011 | Kateraas et al. |
| 2011/0208027 A1 | 8/2011 | Wagner et al. |
| 2011/0213225 A1 | 9/2011 | Bernstein et al. |
| 2011/0257895 A1 | 10/2011 | Brauker et al. |
| 2011/0282327 A1 | 11/2011 | Kellogg et al. |
| 2011/0287528 A1 | 11/2011 | Fern et al. |
| 2011/0289497 A1 | 11/2011 | Kiaie et al. |
| 2011/0320130 A1 | 12/2011 | Valdes et al. |
| 2011/0320167 A1 | 12/2011 | Budiman |
| 2012/0078071 A1 | 3/2012 | Bohm et al. |
| 2012/0088995 A1 | 4/2012 | Fennell et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0190989 A1 | 7/2012 | Kaiser et al. |
| 2012/0245447 A1 | 9/2012 | Karan et al. |
| 2013/0035575 A1 | 2/2013 | Mayou et al. |
| 2013/0184547 A1 | 7/2013 | Taub et al. |
| 2013/0225959 A1 | 8/2013 | Bugler |
| 2013/0231541 A1 | 9/2013 | Hayter et al. |
| 2013/0235166 A1 | 9/2013 | Jones et al. |
| 2013/0324823 A1 | 12/2013 | Koski et al. |
| 2014/0005499 A1 * | 1/2014 | Catt .................... A61B 5/7246 600/301 |
| 2014/0012118 A1 * | 1/2014 | Mensinger .......... A61B 5/6898 600/365 |
| 2014/0046160 A1 | 2/2014 | Terashima et al. |
| 2014/0121480 A1 | 5/2014 | Budiman et al. |
| 2014/0121488 A1 | 5/2014 | Budiman |
| 2015/0141770 A1 | 5/2015 | Rastogi et al. |
| 2015/0216456 A1 | 8/2015 | Budiman |
| 2015/0241407 A1 | 8/2015 | Ou et al. |
| 2016/0022221 A1 | 1/2016 | Ou et al. |
| 2016/0342763 A1 * | 11/2016 | Wada ................... A61B 5/7275 |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-1993/006237 | 4/1993 |
| WO | WO-1996/025089 | 8/1996 |
| WO | WO-1996/035370 | 11/1996 |
| WO | WO-2000/049940 | 8/2000 |
| WO | WO-2000/059370 | 10/2000 |
| WO | WO-2001/052935 | 7/2001 |
| WO | WO-2001/054753 | 8/2001 |
| WO | WO-2002/016905 | 2/2002 |
| WO | WO-2003/076893 | 9/2003 |
| WO | WO-2003/082091 | 10/2003 |

(56) References Cited

FOREIGN PATENT DOCUMENTS

| WO | WO-2004/047445 | 6/2004 |
|----|----------------|--------|
| WO | WO-2005/010756 | 2/2005 |
| WO | WO-2005/040404 | 5/2005 |
| WO | WO-2006/024671 | 3/2006 |
| WO | WO-2006/051466 | 5/2006 |
| WO | WO-2006/064397 | 6/2006 |
| WO | WO-2007/007459 | 1/2007 |
| WO | WO-2007/097754 | 8/2007 |
| WO | WO-2010/022387 | 2/2010 |
| WO | WO-2010/077329 | 7/2010 |
| WO | WO-2012/010298 | 1/2012 |

OTHER PUBLICATIONS

Tsalikian, et al. "Impact of Exercise on Overnight Glycemic Control in Children with Type 1 Diabetes", J Pediatr., 147(4):528-534 (2005).

McMahon, et al. "Glucose Requirements to Maintain Euglycemia after Moderate-Intensity Afternoon Exercise in Adolescents with Type 1 Diabetes Are Increased in a Biphasic Manner", The Journal of Clinical Endocrinology & Metabolism, 92(3):963-968 (2007).

Metcalf, et al. "Effects of Moderate-to-Vigorous Intensity Physical Activity on Overnight and Next-Day Hypoglycemia in Active Adolescents With Type 1 Diabetes", Diabetes Care, 37:1272-1278 (2014).

Bunescu et al., "Blood Glucose Level Prediction Using Physiological Models and Support Vector Regression," 2013 12th International Conference on Machine Learning and Applications, Miami, FL, USA, 2013, pp. 135-140.

Eren-Oruklu M, et al., "Adaptive System Identification for Estimating Future Glucose Concentrations and Hypoglycemia Alarms," Automatica (Oxf) 48(8):1892-1897 (2012).

Georga E, et al., "Multivariate Prediction of Subcutaneous Glucose Concentration in Type 1 Diabetes Patients Based on Support Vector Regression," IEEE J Biomed Health Inform. 17(1):71-81 (2013).

European Patent Application No. 16824962.1, Extended European Search Report dated Feb. 11, 2019.

PCT Application No. PCT/US2016/041632, International Search Report and Written Opinion of the International Searching Authority, dated Oct. 26, 2016.

Armour, J. C., et al., "Application of Chronic Intravascular Blood Glucose Sensor in Dogs", Diabetes, vol. 39, 1990, pp. 1519-1526.

Arnold, M. A., et al., "Selectivity Assessment of Noninvasive Glucose Measurements Based on Analysis of Multivariate Calibration Vectors", Journal of Diabetes Science and Technology, vol. 1, No. 4, 2007, pp. 454-462.

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1070.

Bennion, N., et al., "Alternate Site Glucose Testing: A Crossover Design", Diabetes Technology & Therapeutics, vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Boyne, M. S., et al., "Timing of Changes in Interstitial and Venous Blood Glucose Measured With a Continuous Subcutaneous Glucose Sensor", Diabetes, vol. 52, Nov. 2003, pp. 2790-2794.

Bremer, T. M., et al., "Benchmark Data from the Literature for Evaluation of New Glucose Sensing Technologies", Diabetes Technology & Therapeutics, vol. 3, No. 3, 2001, pp. 409-418.

Brooks, S. L., et al., "Development of an on-Line Glucose Sensor for Fermentation Monitoring", Biosensors, vol. 3, 1987/88, pp. 45-56.

Cass, A. E., et al., "Ferrocene-Mediated Enzyme Electrode for Amperometric Determination of Glucose", Analytical Chemistry, vol. 56, No. 4, 1984, 667-671.

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Eren-Oruklu, M., et al., "Estimation of Future Glucose Concentrations with Subject-Specific Recursive Linear Models", Diabetes Technology & Therapeutics vol. 11(4), 2009, pp. 243-253.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004, pp. 1.

Garg, S., et al., "Improvement in Glycemic Excursions with a Transcutaneous, Real-Time Continuous Glucose Sensor", Diabetes Care, vol. 29, No, 1, 2006, pp. 44-50.

Hovorka, R., et al., "Nonlinear Model Predictive Control of Glucose Concentration in Subjects with Type 1 Diabetes", Physiological Measurement, vol. 55, Jul. 2004, pp. 905-920.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Kovatchev, B. P., et al., "Graphical and Numerical Evaluation of Continuous Glucose Sensing Time Lag", Diabetes Technology & Therapeutics, vol. 11, No. 3, 2009, pp. 139-143.

Kuure-Kinsey, M., et al., "A Dual-Rate Kalman Filter for Continuous Glucose Monitoring", Proceedings of the 28th IEEE, EMBS Annual International Conference, New York City. 2006, pp. 63-66.

Li, Y., et al., "In Vivo Release From a Drug Delivery MEMS Device", Journal of Controlled Release, vol. 100, 2004, pp. 211-219.

Lo, B., et al., "Key Technical Challenges and Current Implementations of Body Sensor Networks", Body Sensor Networks, 2005, pp. 1-5.

Lodwig, V., et al., "Continuous Glucose Monitoring with Glucose Sensors: Calibration and Assessment Criteria", Diabetes Technology & Therapeutics, vol. 5, No. 4, 2003, pp. 573-587.

Lortz, J., et al., "What is Bluetooth? We Explain the Newest Short-Range Connectivity Technology", Smart Computing Learning Series, Wireless Computing, vol. 8, Issue 5, 2002, pp. 72-74.

Malin, S. F., et al., "Noninvasive Prediction of Glucose by Near-Infrared Diffuse Reflectance Spectroscopy", Clinical Chemistry, vol. 45, No. 9, 1999, pp. 1651-1658.

McGarraugh, G., et al., "Glucose Measurements Using Blood Extracted from the Forearm and the Finger", TheraSense Inc., 2001, 16 Pages.

McGarraugh, G., et al., "Physiological Influences on Off-Finger Glucose Testing", Diabetes Technology & Therapeutics, vol. 3, No. 3, 2001, pp. 367-376.

McKean, B. D., et al., "A Telemetry—Instrumentation System for Chronically Implanted Glucose and Oxygen Sensors", IEEE Transactions on Biomedical Engineering, vol. 35, No. 7, 1988, pp. 526-532.

(56) References Cited

OTHER PUBLICATIONS

Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.

Mougiakakou, et al., "A Real Time Simulation Model of Glucose-Insulin Metabolism for Type 1 Diabetes Patients", Proceedings of the 2005 IEEE, 2005, pp. 298-301.

Panteleon, A. E., et al., "The Role of the Independent Variable to Glucose Sensor Calibration", Diabetes Technology & Therapeutics, vol. 5, No. 3, 2003, pp. 401-410.

Parker, R., et al., "Robust H∞ Glucose Control in Diabetes Using a Physiological Model", AIChE Journal, vol. 46, No. 12, 2000, pp. 2537-2549.

Pickup, J., et al., "Implantable Glucose Sensors: Choosing the Appropriate Sensing Strategy", Biosensors, vol. 3, 1987/88, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155-E161.

Roe, J. N., et al., "Bloodless Glucose Measurements", Critical Review in Therapeutic Drug Carrier Systems, vol. 15, Issue 3, 1998, pp. 199-241.

Sakakida, M., et al., "Development of Ferrocene-Mediated Needle-Type Glucose Sensor as a Measure of Tme Subcutaneous Tissue Glucose Concentrations", Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry—Instrumentation System for Long-Term Implantable Glucose and Oxygen Sensors", Analytical Letters, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Glycaemic Control in Pancreatectomized Dogs with a Wearable Artificial Endocrine Pancreas", Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shichiri, M., et al., "Wearable Artificial Endocrine Pancreas With Needle-Type Glucose Sensor", The Lancet, 1982, pp. 1129-1131.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Steil, G. M., et al., "Closed-Loop Insulin Delivery—the Path of Physiological Glucose Control", Advanced Dmg Delivery Reviews, vol. 56, 2004, pp. 125-144.

Steil, G. M., et al., "Determination of Plasma Glucose During Rapid Glucose Excursions with a Subcutaneous Glucose Sensor", Diabetes Technology & Therapeutics, vol. 5, No. 1, 2003, pp. 27-31.

Sternberg, R., et al., "Study and Development of Multilayer Needle-Type Enzyme-Based Glucose Microsensors", Biosensors, vol. 4, 1988, pp. 27-40.

Thompson, M., et al., "In Vivo Probes: Problems and Perspectives", Clinical Biochemistry, vol. 19, 1986, pp. 255-261.

Turner, A., et al., "Diabetes Mellitus: Biosensors for Research and Management", Biosensors, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.

Velho, G., et al., "Strategies for Calibrating a Subcutaneous Glucose Sensor", Biomedica Biochimica Acta, vol. 48, 1989, pp. 957-964.

Wilson, G. S., et al., "Progress Toward the Development of an Implantable Sensor for Glucose", Clinical Chemistry, vol. 38, No. 9, 1992, pp. 1613-1617.

* cited by examiner

FIG. 13

SYSTEM, DEVICE AND METHOD OF DYNAMIC GLUCOSE PROFILE RESPONSE TO PHYSIOLOGICAL PARAMETERS

RELATED APPLICATIONS

This national stage patent application under 35 U.S.C. § 371 claims priority to PCT Application No. PCT/US16/41632 filed Jul. 8, 2016, which is related to U.S. Provisional Application No. 62/307,346 filed Mar. 11, 2016, U.S. Provisional Application No. 62/191,218 filed Jul. 10, 2015, and to U.S. Provisional Application No. 62/307,344 filed Mar. 11, 2016, entitled "Systems, Devices, and Methods For Meal information Collection, Meal Assessment, and Analyte Data Correlation," the disclosures of each of which are incorporated herein by reference for all purposes.

INCORPORATION BY REFERENCE

Patents, applications and/or publications described herein, including the following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; U.S. Published Application Nos. 2004/0186365, now U.S. Pat. No. 7,811,231; 2005/0182306, now U.S. Pat. No. 8,771,183; 2006/0025662, now U.S. Pat. No. 7,740,581; 2006/0091006; 2007/0056858, now U.S. Pat. No. 8,298,389; 2007/0068807, now U.S. Pat. No. 7,846,311; 2007/0095661; 2007/0108048, now U.S. Pat. No. 7,918,975; 2007/0199818, now U.S. Pat. No. 7,811,430; 2007/0227911, now U.S. Pat. No. 7,887,682; 2007/0233013; 2008/0066305, now U.S. Pat. No. 7,895,740; 2008/0081977, now U.S. Pat. No. 7,618,369; 2008/0102441, now U.S. Pat. No. 7,822,557; 2008/0148873, now U.S. Pat. No. 7,802,467; 2008/0161666; 2008/0267823; and 2009/0054748, now U.S. Pat. No. 7,885,698; U.S. patent application Ser. No. 11/461,725, now U.S. Pat. No. 7,866,026; Ser. Nos. 12/131,012; 12/393,921, 12/242,823, now U.S. Pat. No. 8,219,173; Ser. No. 12/363,712, now U.S. Pat. No. 8,346,335; Ser. Nos. 12/495,709; 12/698,124; 12/698,129, now U.S. Pat. No. 9,402,544; Ser. Nos. 12/714,439; 12/794,721, now U.S. Pat. No. 8,595,607; and Ser. No. 12/842,013, now U.S. Pat. No. 9,795,326, and U.S. Provisional Application Nos. 61/238,646, 61/246,825, 61/247,516, 61/249,535, 61/317,243, 61/345,562, and 61/361,374.

BACKGROUND

The detection and/or monitoring of glucose levels or other analytes, such as lactate, oxygen, A1C, or the like, in certain individuals is vitally important to their health. For example, the monitoring of glucose level is particularly important to individuals with diabetes and those with conditions indicative of onset of diabetes. Diabetics generally monitor glucose levels to determine if their glucose levels are being maintained within a clinically safe range, and may also use this information to determine if and/or when insulin is needed to reduce glucose levels in their bodies or when additional glucose is needed to raise the level of glucose in their bodies.

With the development of glucose monitoring devices and systems that provide real time glucose level information in a convenient and pain-less manner, there is an ongoing desire to integrate such monitoring devices and systems into daily life and activities to improve glycemic control. More specifically, there is a strong desire to identify the impact of daily activities such as exercise, medication administration, meal consumption and so forth on glucose level fluctuation and provide actionable, personalized health related information to tightly control glycemic variations. Furthermore, there is a strong desire to provide accuracy in medication dose determination that accurately assess the correct medication dose determination while reducing errors in such determination by taking into consideration parameters that impact medication therapy in the daily activities including exercise and meal consumption.

SUMMARY

Embodiments of the present disclosure include multi-phase glucose response pattern determination and dynamic adjustment or modification to personalize the glycemic response to the particular activities and external parameters relevant to a specific patient or user. In certain embodiments, an analysis module is provided as a software application ("App") that is executable by any processor controlled device, and in particular, a smart phone with communication capabilities to receive, analyze, transfer, transmit, display or output actionable information, for example, including therapy recommendation based on the determined glucose response pattern. In certain embodiments, the glucose response pattern, determined in view of a particular activity or combinations of activities, meal intake, medication intake, or any other external parameters specific to the daily activities of a user or a patient, is intelligently and dynamically adjusted on an on-going real time basis as additional activity specific or external parameter specific data is received and analyzed by the App.

Embodiments of the present disclosure include an overall network with sensor based devices in communication with the smart phone configured to execute the App, and optionally a data communication network with one or more back-end server terminals providing a network cloud configuration that is configured to either execute the functions of the App for analysis, for example, when in direct data communication with the sensor based devices, and provide the results of the analysis to the smart phone, or configured to operate in a more passive role, such as performing data backup functions or data repository functions for the smart phone and/or the sensor based devices. Also, optionally included in the overall network are one or more medication devices such as an insulin pump or an insulin injector pen that is configured to receive analysis data from the smart phone, from the one or more back-end server terminals, or directly from the sensor based devices.

Embodiments of the present disclosure include a data collection phase during which user or patient specific information is collected from one or more of the sensor based devices, by manual user input, or from a medication delivery device, for example, over a predetermined time period. When it is determined that sufficient amount of information about the patient or the user as it relates to glucose response and glycemic variation (for example, a minimum of 5 days, 6 days, one week, 10 days, 14 days, or any one or more combination of the number of days or portions of days), the App executed on the smart phone in certain embodiments may prompt the user or the patient that a specific glycemic response pattern has been determined or identified and is ready for user input for response analysis. To reach this point, in certain embodiments, the App analyzes data or information from the sensor based devices and other received user or patient specific parameters, and categorizes the received data, as part of the data analysis to determine the glucose response pattern, and thereafter continuously and dynamically updates the response pattern with the additional real time information received from the one or more sensor based devices or other user or patient specific parameters. In this manner, in certain embodiments, when the user inputs an activity or a parameter that the user wishes to engage in (for example, a 90 minute run that includes approximately 1,000 feet of incline, or number of steps taken during an established time period such as 12 hours, 18 hours, 24 hours, or other suitable time periods), the App, using the dynamic glucose response pattern recognition capabilities, is configured to notify the user or the patient that such activity will result in a specific glucose response (for example, a reduction in the glucose level, post activity, of approximately 25 mg/dL).

Further, in certain embodiments, the App may be configured to provide recommendations in addition to the physical activity driven analysis performed, such as, for example, provide a list of food type and amount to be consumed at a particular time prior to engaging in the activity, and/or within a fixed time post-activity so as to minimize glycemic fluctuation exceeding a predetermined range over a set time period spanning from prior to the activity, during, and post activity. In certain embodiments, the App is configured to perform similar analysis described above with recommendations where instead of the physical activity to be performed, the analysis relates to the amount of medication, food, drink, or one or more combinations thereof, to be consumed. In this manner, in certain embodiments, the user or the patient can take actions before consuming food and/or drinks or administering medication.

These and other features, objects and advantages of the present disclosure will become apparent to those persons skilled in the art upon reading the details of the present disclosure as more fully described below.

BRIEF DESCRIPTION OF THE DRAWINGS

FIG. 13 is a graph showing R values in accordance with the one embodiment of the present disclosure.

DETAILED DESCRIPTION

Before the present disclosure is described in detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Figure 1:
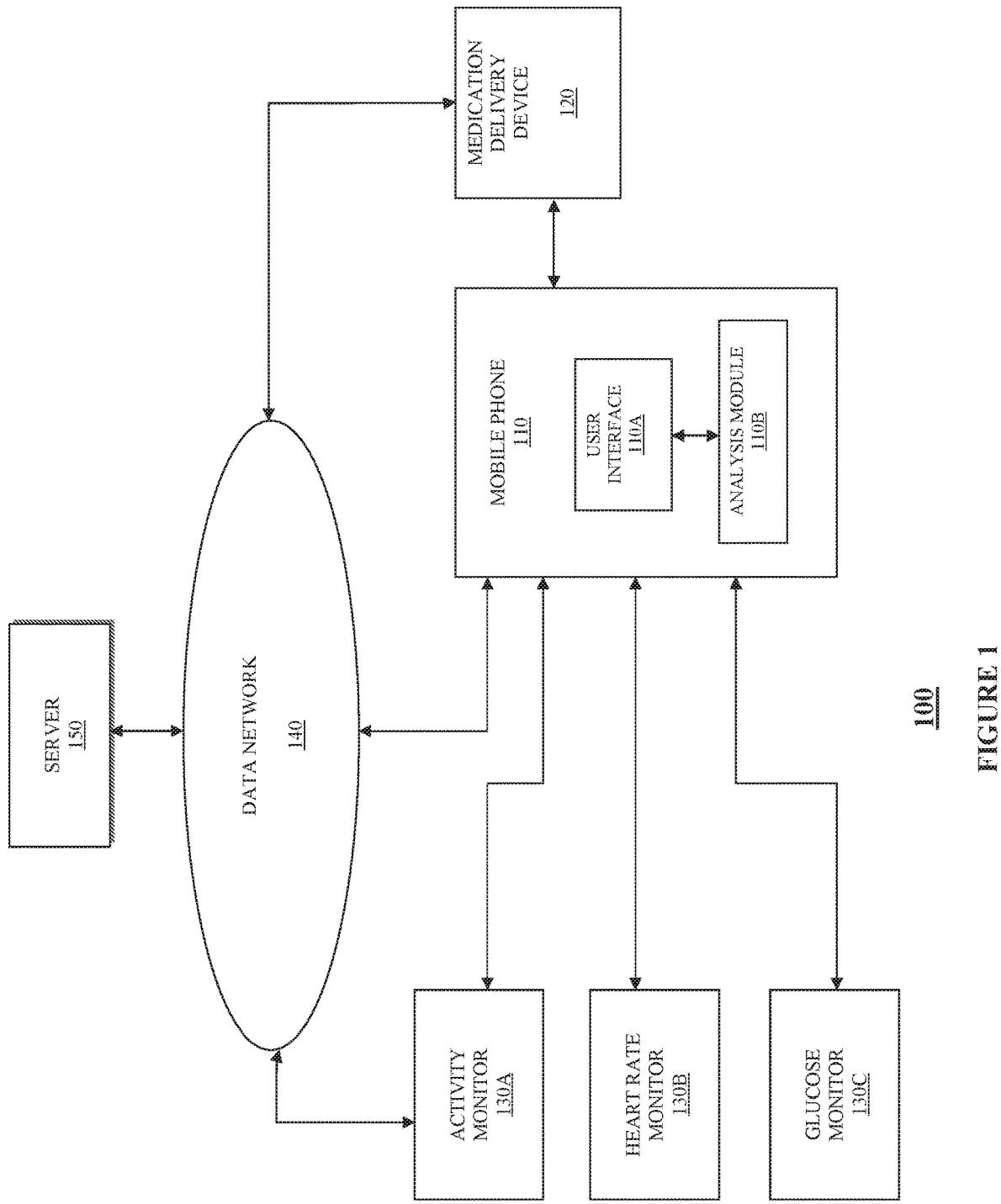
FIG. 1 is an overall glucose response data analysis system in accordance with one embodiment of the present disclosure.

FIG. 1 is an overall glucose response data analysis system in accordance with one embodiment of the present disclosure. Referring to the Figure, glucose response data analysis system 100, in certain embodiments, includes a mobile phone 110 including user interface 110A and analysis module 110B programmed in the mobile phone 110 as an App, for example, installed as a downloaded executable file over data network 140 from server 150. As discussed in further detail below, in certain embodiments, data conditioning, analysis and dynamic glucose response pattern recognition and/or updating the glucose response pattern recognition is implemented as one or more executable routines by the App.

Referring back to FIG. 1, also shown are activity monitor 130A, heart rate monitor 130B, and glucose monitor 130C each in data communication with the mobile phone 110, or alternatively or in addition to, each in data communication with server 150 over data network 140. In this manner, each monitor 130A, 130B, 130C, in certain embodiments, is programmed to communicate the monitored information to server 150 for storage and/or analysis, or to mobile phone 110 for storage, analysis, and subsequent communication of either or both raw data received from each monitor 130A, 130B, 130C, and/or processed data or information from each monitor 130A, 130B, 130C to server 150 over data network for storage and/or further analysis.

Referring still to FIG. 1, also shown in glucose response data analysis system 100 is medication delivery device 120 in data communication with mobile phone 110, server 150, or one or more of the monitors 130A, 130B, 130C over data network 140. While not shown, in certain embodiments, the operation of the routines and functions of the App may be implemented in medication delivery device 120 where medication delivery device 120 directly receives data or information from one or more of the monitors 130A, 130B, 130C, and performs glucose response pattern recognition and analysis, and, for example, modifies a medication delivery profile (e.g., basal insulin delivery rate, determine a bolus insulin dose amount) based on the determined glucose response pattern from the monitored data (e.g., physiological monitored condition, and/or consumption of food and/or drinks, and medication intake) in view of the proposed physical activity and/or food or drink consumption.

In certain embodiments, mobile phone 110 includes one or more monitors 130A, 130B, 130C integrated within the phone 110. For example, mobile phone 110, in certain embodiments, includes an accelerometer and/or gyroscope that can monitor the movement of the mobile phone 110 user, such as keeping track or recording the number of steps taken, physical activities engaged (while having the mobile phone 110 on or close to the body such as using an arm band) such as number of steps taken, runs, jogs, sprints, each with a degree or level of intensity. In certain embodiments, mobile phone 110 is provided as a wrist watch configuration in which case mobile phone 110 includes a heart rate monitor in addition to the accelerometer or the gyroscope. In certain embodiments with the mobile phone 110 configured as a wrist watch, the mobile phone 110 incorporates a glucose sensor—in vivo, dermal, transdermal, or optical, such that the real time monitoring function of the glucose level is incorporated into the mobile phone 110.

Referring still again to glucose response data analysis system 100, in certain embodiments, a hub device (not shown) may be incorporated into the system 100, which is configured to communicate with one or more of the monitors 130A, 130B, 130C for data reception, storage, and subsequent communication to other devices in the system 100 over data network 140, or in direct communication with other devices in the system 100 such as, for example, mobile phone 110 and/or medication delivery device 120. The hub device, in certain embodiments, is configured as a pass through relay device or adapter that collects information from one or more of the monitors 130A, 130B, 130C, and either in real time or after a certain time period of data collection, transfers or sends the collected data to server 150, to mobile phone 110, and/or to medication delivery device 120. In certain embodiments, hub device is physically embodied as a small, discreet key fob type or dongle type device which the user or the patient keeps close to the body and communicates directly with monitors 130A, 130B, 130C worn on the body. Further, while three monitors 130A, 130B, 130C are shown in glucose response data analysis system 100, within the scope of the present disclosure additional sensors are provided to monitor other or related parameters of the user. For example, parameters for monitoring or measuring by one or more sensors include, but are not limited to, perspiration level, temperature level, heart rate variability (HRV), neural activity, eye movement, speech, and the like. Each one or more of these monitored parameters in certain embodiments of glucose response data analysis system 100 is used as input parameter to the analysis module 110B of mobile phone 110 as discussed in further detail below.

Figure 2A:
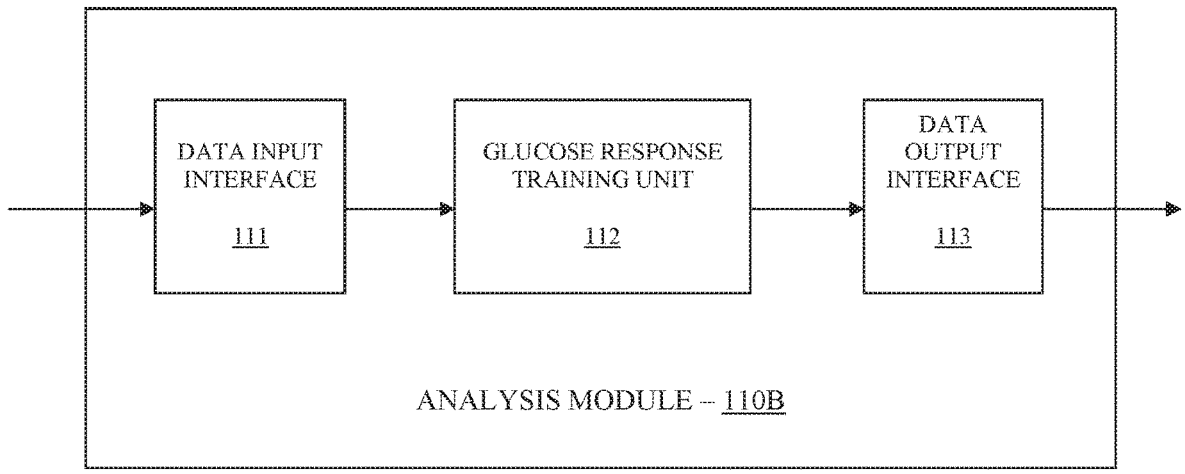
FIG. 2A is a block diagram of the analysis module of FIG. 1 in accordance with one embodiment of the present disclosure.

FIG. 2A is a block diagram of the analysis module 110B of FIG. 1 in accordance with one embodiment of the present disclosure. As shown in certain embodiments, analysis module 110B of mobile phone 110 includes data input interface 111 for interfacing or receiving data input from one or more 130A, 130B, 130C monitors external to mobile phone 110 or internal and within mobile phone 110. Data and/or information received via data input interface are provided to glucose response training unit 112. In certain embodiments, glucose response training unit 112 categorizes the received input data into respective categories depending upon the type of data, and the type or types of parameter associated with the data. For example, if the type of data is associated with a physical activity such as a 90 minute run, the parameters associated with the data include, in addition to duration, the level of run intensity (run, jog, sprint) which, in certain embodiments, may be determined using monitored heart rate information (if available) or pace of the run, aerobic or anaerobic run, competitive or non-competitive (training)

run, or any other suitable category associated with the physical activity (e.g., the run). In certain embodiments, other type of data associated with the physical activity can be used such as number of steps taken during an established time period.

With the categorized data received from the one more monitors 130A, 130B, 130C (FIG. 1), the time corresponding glucose level information is retrieved (or received from glucose monitor 130C (FIG. 1)), and glucose response training unit 112 performs dynamic glucose response pattern recognition based, for example, on the analysis tools provided in the App for execution on mobile phone 110. Further, in certain embodiments, glucose response training unit 112 is configured to dynamically and continuously update the determined glucose response pattern based on the real time information from the one or more monitors (FIG. 1).

In certain embodiments, the accuracy of the glucose response pattern improves with increased data set over a longer time period (and/or with higher resolution/monitored frequency). However, a person's glycemic response to inputs may change over time. Certain embodiments address this by "resetting" or clearing the data set after some predetermined time period has elapsed. In other embodiments, the App recognizes that exceeding a set data collection duration potentially introduces error in accuracy of the glucose response pattern, in which case, when this point in time has reached, the App is configured to reset and enter the data collection period during which user driven analysis of glucose response feedback is disabled for at least the minimum number of days or hours for which monitored data is necessary to analyze and determine a new glucose response pattern. As described in further detail below, in certain embodiments, the App is configured to establish a "forgetting" window during which user driven analysis of glucose response feedback is continuously updated. The "forgetting" window, in certain embodiments, includes one or more of a predetermined time period set by the App or based on user input, or alternatively, is dynamically modified based on the glucose response feedback.

Referring back to FIG. 2A, in certain embodiments, the output of glucose response training unit 112 is provided to data output interface 113 which is operatively coupled to user interface 110A of mobile phone 110 for display, output or otherwise notification or prompt to the user of mobile phone 110 that the App has completed the initial or preliminary analysis and is operational to analyze glucose response to inputs such as number of steps taken, bike rides, runs, hikes, meals, for which the user or patient wishes to identify the corresponding glucose response so as to take timely action (corrective or proactive) to maintain glycemic control and minimize undesirable glucose fluctuations.

FIG. 2A illustrates the information flow in conjunction with the analysis module 110B of FIG. 1 performing data categorization, pattern recognition and dynamic update in accordance with one embodiment of the present disclosure. Referring to FIG. 2A, in certain embodiments, analysis module 110B of mobile phone 110 (FIGS. 1, 2A) executing the App is configured to categorize (220) the received input data (210), such as for example, type of activity, intensity level, duration, location, altitude information, glucose level, heart rate information, heart rate variability (HRV) information, oxygen saturation level, perspiration level, temperature level, medication intake information, type of medication, medication administration duration, time of day information corresponding to the administration of medication, carbohydrate intake information, alcohol consumption information or any other related metric for the particular monitored condition corresponding to the input data received.

With the received information, in certain embodiments, glucose response training unit 112 (FIG. 2A) performs dynamic glucose response pattern recognition and updates to the pattern (220) as new or additional data is received. As discussed in further detail below, in certain embodiments, prior to the output of the glucose response profile (230) based on the determined pattern, glucose response training unit 112 of analysis module 110B in mobile phone 110 ensures that sufficient input data has been analyzed. Once this point has reached and monitored information over at least a minimum time duration has been received and analyzed, the App, in certain embodiments, is configured to generate a notification to the user (for example, as an output prompt on the user interface 110A of mobile phone 110) when it determines information that may be useful to the user. Notifications may be made automatically, such as an alarm notification; or retrieved by the user when using the App, such as accessing the information from a menu; or displayed when the user next interacts with the App. An example of useful information is that the user's glucose levels are typically 20% lower overnight after they exercise during the prior day. The user can use this information to make sure that they do not experience night time hypoglycemia, for instance, by reducing their insulin coverage during this time or by having a snack before bedtime.

In another aspect of the present disclosure, the App prompts the user to enter contextual information when it detects certain conditions that warrant more information to be entered. The information entered is used by the routine that analyzes the input data to determine glycemic response patterns. The App contains routines that detect conditions, for instance, when meals have occurred or when activity has occurred, and notifies the user when these conditions are detected. Embodiments of the user notification includes one or more of an icon display, auditory or text output notification, or vibratory notification configured to prompt the user to provide more information about the condition that was detected. Examples of the one or more conditions include detected movement, detected rate of change of glucose increase or decrease exceeding or accelerating beyond a set threshold, detected spike or change in heart rate, perspiration or temperature level. Alternatively, rather than an alarm type notification, the App may provide the notification when the user next interacts with the App or the smartphone.

Referring yet again to the Figures, glucose response training unit 112 of analysis module 110B, in certain embodiments, is configured to perform dynamic glucose response pattern recognition based on glucose metrics that characterize the impact of a particular activity or event for a specific user or a patient, for example, impact of a particular activity or event (meal or medication intake, for example) for specific time of day periods that occur during and after an activity. Different glucose metrics such as mean or median glucose level can be used as the glucose metric. In certain embodiments, the use of median glucose information is less susceptible to outlier glucose data as compared to mean glucose level.

In certain embodiments, the glucose response training unit 112 determines the median of the continuously monitored glucose level during an overnight period after a particular activity, such as from 10 pm to 3 am, or from 3 am to 8 am, or from 10 pm to 8 am, for example. In certain embodiments, the glucose response training unit 112 uses the median glucose level determined during the day time periods, such as from 8 am to 10 pm, from 8 am to 6 pm, from 9 am to 5 pm, from 5 pm to 10 pm, or any other suitable day time period ranges. In certain embodiments, the median glucose information is determined with reference to a particular activity such that the median glucose level is determined for period of time after the start of the activity (2 hours after start of activity) for specific time duration (e.g., 12 hours). In certain embodiments, the relative start time for determining median glucose level and the duration of time period varies depending on the type of activity and/or other parameters related to the activity or associated with the user or the patient.

While the embodiments disclosed focus on activity during the daytime period impacting glucose levels at night, within the scope of the present disclosure similar analysis applies to any time periods defined by fixed times-of-day, such as activity in the morning (e.g., 5 am to 12 pm) impacting glucose levels post-dinner (e.g., 6 pm to 10 pm). Alternatively, the analysis disclosed herein within the scope of the present disclosure is applied to periods defined by events that occur regularly. For instance, the activity data set are generated from time periods defined each day as 5 am to breakfast where breakfast is a different time every day and determined by a user-entered or generated indication, or by an algorithm that processes glucose data to determine meal starts or by a recorded rapid acting insulin infusion. Exemplary embodiments of algorithmically detecting meal starts are disclosed in WO 2015/153482 (having International Application No. PCT/US2015/023380, filed Mar. 30, 2015), assigned to the Assignee of the present application, and the disclosure of which is incorporated by reference in its entirety for all purposes.

Further, the impacted time period may be defined likewise as the time period starting at when a meal is detected, such as the start of dinner until midnight. Also, within the scope of the present disclosure, a hybrid approach is provided where the activity time period is determined as a fixed time-of-day period while the impacted time period is determined by particular meal start times. Within the scope of the present disclosure, the impact on multiple time periods, such as post-breakfast, post-lunch, post-dinner and overnight are included. Further, the analysis can be extended to time periods across multiple days; for instance, determining how an activity occurring in a morning period of a first day impacts glucose levels on a subsequent day.

Figure 3:
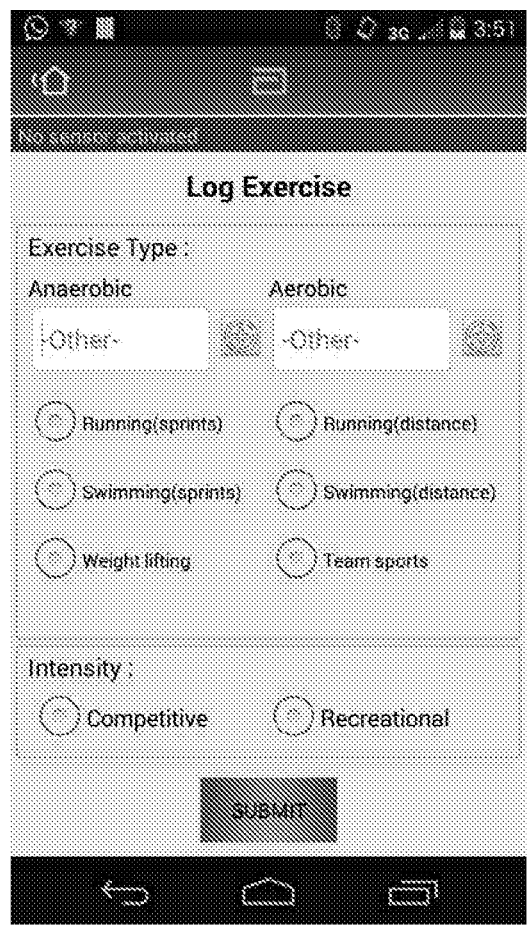
FIG. 3 is an exemplary screenshot of the data input interface 111 (FIG. 2A) in accordance with one embodiment of the present disclosure.

In addition, within the scope of the present disclosure two or more activity types can be used for analysis. A nonlimiting example requires a) users to enter into the user interface (UI) of the App (e.g., data input interface 111 of analysis module 110B (FIG. 2A)) contextual information related to the activities they perform, or b) using one or more sensors to differentiate between different types of activities, or c) alternative detection technology to differentiate between different types of activities. For user entered information approach (a) above, the App is configured to present a user interface (as shown in FIG. 3, for example) to allow users to enter activity information. In certain embodiments, users can enter information from a checklist or free-text entry. In addition, the App is configured to detect when measured activity exceeded a predefined threshold and prompt the user to enter this information. For the approach using one or more sensors to detect different activities (approach (b)), a combination of pedometer, heart rate sensor, and location sensor can be used where one or more thresholds and defined logic are configured to identify body motion, intensity, and speed and altitude change. Finally, for the approach using alternative detection technology (approach (c)), a location sensor may be used, for instance, to detect when the user is at the weightlifting gym, so that activity measured can be associated with anaerobic activity.

When an activity type attribute is associated with a measured activity metric, the analysis described below can be performed for each activity type. For example, if two activity types are used, such as aerobic and anaerobic, the analysis described below can be used to determine the impact of aerobic activity on future glucose levels, and independently determine the impact of anaerobic activity on future glucose levels. Within the scope of the present disclosure, one or more combinations of activities and analysis time periods can be achieved such as days with both types of activity indicating a new type of activity.

In certain embodiments, glucose response training unit 112 determines glucose median level, activity and other related parameters for multiple daytime periods and median glucose level is determined for associated overnight periods that follow the daytime periods. In certain embodiments, glucose response training unit 112 determines glucose median levels for the time of day periods for days without activity. More specifically, glucose response training unit 112, in certain embodiments, is configured to confirm with the user or patient that significant activity (e.g., an exercise event, number of steps taken during a day time period (12 hours, 18 hours, 24 hours, or other suitable time periods), a run, bike ride, hike, etc.) did not occur during these days without significant activity. With time periods separated between those days with significant activity and those days without significant activity, glucose response training unit 112, in certain embodiments, analyzes the received input data (see FIG. 2A) to characterize the impact of particular activities on overnight glucose level to generate the dynamic glucose response pattern—that is, to assess how the user or patient's body reacts to the specific activities, and to generate or provide appropriate therapy recommendation to the user or the patient when the user decides to engage in the same activities with the same or similar parameters such as duration, level of intensity and the like.

FIG. 3 is an exemplary screenshot of the data input interface 111 (FIG. 2A) in accordance with one embodiment of the present disclosure. Referring to FIG. 3, in certain embodiments, customized data entry screen is presented to the user for information entry for analysis by the App. In a nonlimiting example, a set of radio buttons on the user interface (of the mobile telephone executing the App, for example) are seeded with one or more default activity related parameters such as number of steps, run, jog, hike, bike ride, swim, sleep, and/or food/drink related parameters such as coffee, alcohol with sugar, alcohol without sugar, cereal, bacon, toast, and the like, with the option to modify over time as new custom answers/feedback or responses are added by the user. This allows the user to quickly enter the most common or most used types of activity without losing the flexibility to enter other types of custom data.

Within the scope of the present disclosure, the App provides multiple means for users or patients to enter information about meals and activity. The patient can proactively enter this information. This is particularly useful for meal entry where a photo of the meal can be entered. This may be a much more convenient and fun way for users or patients to enter and view meals information. Additional details can be found in Provisional Patent Application No. 62/307,344 entitled "Systems, Devices, and Methods For Meal Information Collection, Meal Assessment, and Analyte Data Correlation" filed concurrently herewith. As discussed above, in certain embodiments, the App may detect a meal or activity episode and prompt the patient for more information as disclosed in WO 2015/153482 incorporated by reference in its entirely for all purposes.

For users or patients that use insulin or take other glucose-altering medications, the App may be configured to automatically retrieve user/patient specific data regarding use of these medications or allow manual patient entry into the system.

Within the scope of the present disclosure, the App is configured to facilitate experimentation and understanding by providing a meal/activity analysis output. In certain embodiments, the output is presented as one or more reports on the smartphone or on a web browser retrieved from a server. The one or more reports list meal episodes as defined by glucose excursions. The list of meal episodes can be sorted by date-time of the episode, or by severity of the glucose excursion, such as measured by peak glucose level, by glucose change over the course of the excursion, or by area defined by glucose and duration of the excursion. Each row in the analysis output report(s) includes information associated with the meal episode. In certain embodiments, the report(s) includes one or more of the photos or otherwise text entries associated with that meal episode, date-time, and one or more meal severity metrics. The report(s), in certain embodiments, also includes any related activity information within some period of time of the meal. Too much information on this list may be too cluttered to be practical. Thus, the App, in certain embodiments, provides the user or the patient to manipulate the presentation of information, such as selecting the row and presenting a popup window with a more detailed information screen. Such detailed information screen also provides a glucose plot associated with the meal episode. In this manner, meals that have the most impact on glucose levels can be highlighted in an easy to view presentation to provide a better understanding of the impact of certain foods on their glucose levels so that the user or the patient can avoid or limit foods that are detrimental to their health.

The App, in certain embodiments, is also configured to learn how food and activity can impact future glucose levels. When food and activity are selected on the customizable checklist described above, glucose data are associated with these selections and multiple glucose datasets can be associated with a single entry type. Also, multiple glucose datasets can be associated with combinations of one or more meal entry types and one or more activity entry types. The glucose datasets may be processed in one or more different manners in order to characterize the impact of the episode on glucose levels.

In certain embodiments, the median glucose levels from all of the data sets are determined and compared to the median of all periods of captured glucose data. Alternatively, this approach can be applied to individual time-of-day periods, such as pre-breakfast, post-breakfast, post-lunch, post-dinner and post-bedtime. Over time, the App is configured to estimate with some level of confidence the glycemic impact for any given entry type or combination of entry types. For instance, a specific activity type "bike ride uphill" for 1 or more hours of activity may be associated with a 20% increase in patient insulin sensitivity for the next 24 hours—the change in insulin resistance is readily associated with the change in median glucose. This association may be made by the system when the system detects that the statistical level of confidence has exceed some predetermined amount. This information may alter the parameters used in bolus calculator over the next 24 hours. Alternatively, the App may detect activity associated with the bike ride and alert the patient, for instance, at bedtime so they can have a snack to avoid hypoglycemia that night.

Another type of output report presented by the App includes a list of activities that can be sorted by median glucose levels over the period of time following the activity, such as 24 hours. The list can illustrate which activities have the biggest impact on future glucose levels. Further, another type of report can present a list of food and activity combinations, in the same way as described. These approaches can be readily extended to other sensor data and other contextual inputs, such as illness, alcohol consumption, coffee consumption, and the like.

Figure 4:
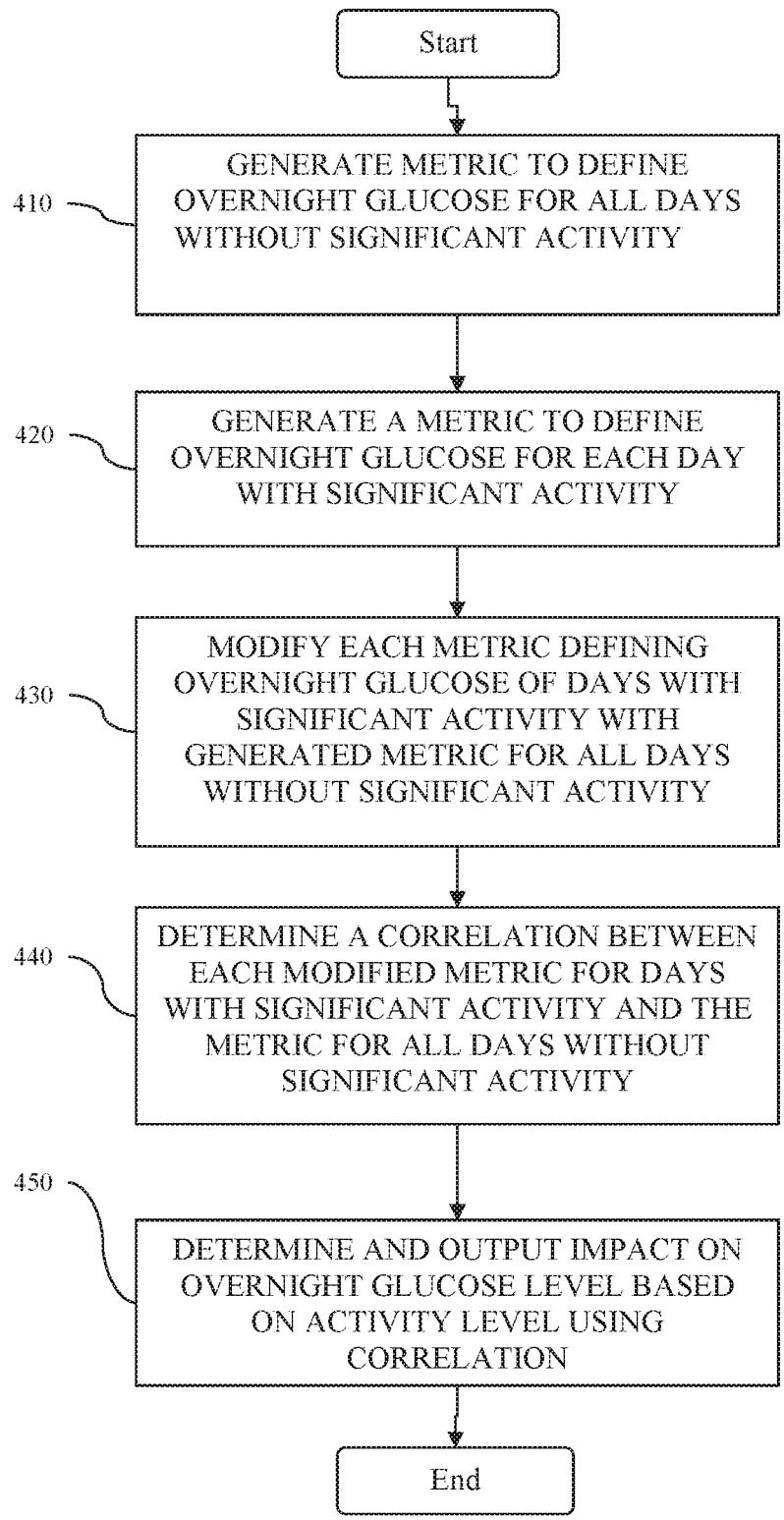
FIG. 4 is a flowchart illustrating a routine to determine the impact of day time activity on overnight glucose level in accordance with one embodiment of the present disclosure.

FIG. 4 is a flowchart illustrating a routine to determine the impact of day time activity on overnight glucose level in accordance with one embodiment of the present disclosure. Referring to FIG. 4, in one embodiment, determining the impact of day time activity on overnight glucose level includes generating a metric to define an overnight glucose level for all days without significant activity over a predetermined time period (e.g., 2 weeks, a month, or any other suitable time period) (410). Thereafter, a metric is generated to define the overnight glucose level for each day with significant activity in the predetermined time period (420). Within the scope of the present disclosure the determination of days with or days without significant activity is based on one or more activity metric exceeding a defined threshold (e.g., number of steps exceeding a threshold within a 24 hour time period). Referring back to FIG. 4, after generating the metric to define overnight glucose level for all days without significant activity, and a plurality of metrics to define the overnight glucose level for each day with significant activity, each of the plurality of metrics to define the overnight glucose level for each day with significant activity is modified with the metric for all days without significant activity (430). Then, a correlation is determined between each modified metric for days with significant activity and the metric for all days without significant activity (440), and thereafter, given an activity level, the impact on the overnight glucose level of the activity level is determined and presented to the user based on the determined correlation (450).

Figure 5:
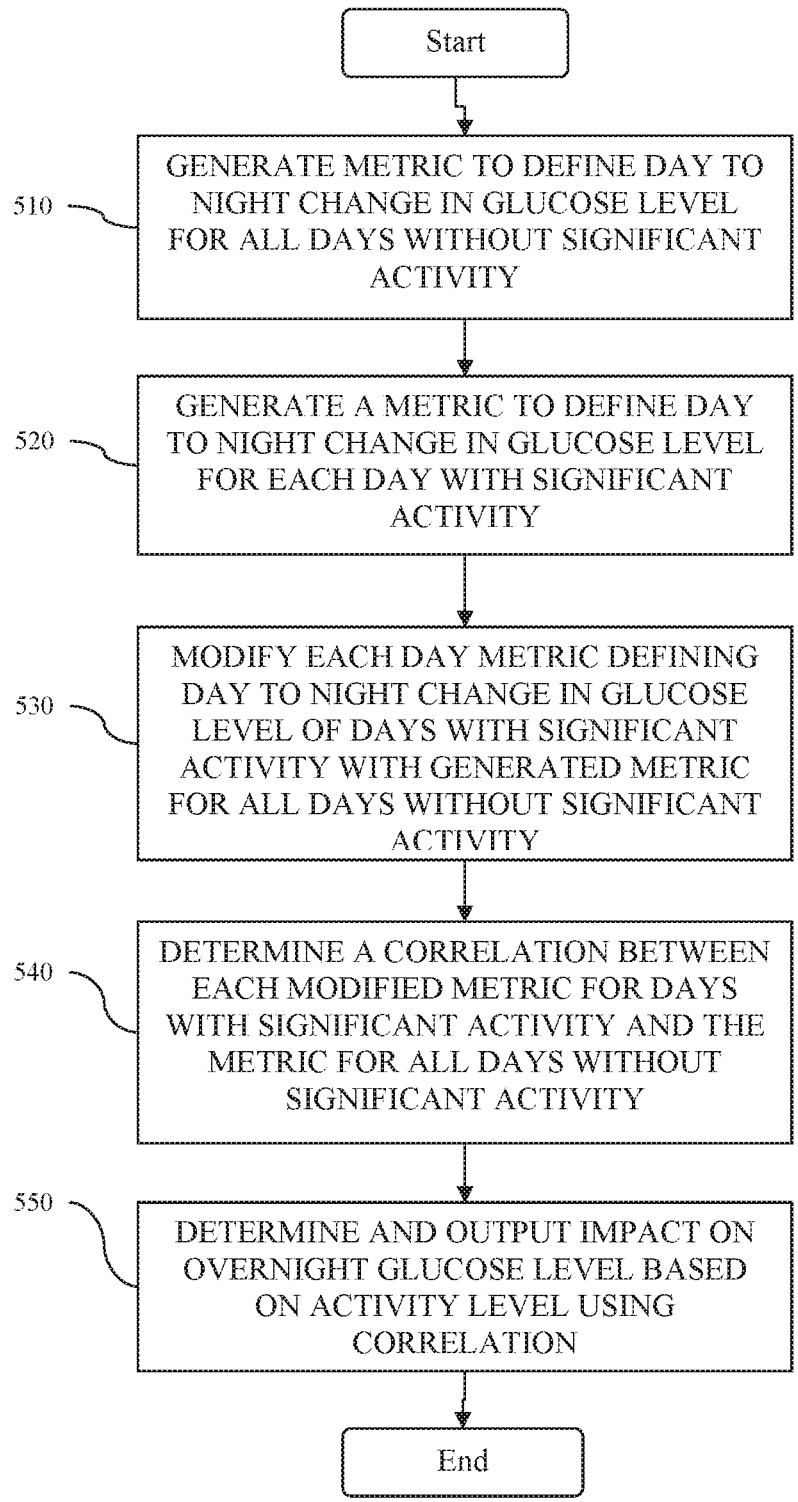
FIG. 5 is a flowchart illustrating another routine to determine the impact of day time activity on overnight glucose level in accordance with one embodiment of the present disclosure.

FIG. 5 is a flowchart illustrating another routine to determine the impact of day time activity on overnight glucose level in accordance with one embodiment of the present disclosure. Referring to FIG. 5, in one embodiment, determining the impact of day time activity on overnight glucose level includes generating a metric to define a day-to-night change in glucose level for all days without significant activity over a predetermined time period (for example, 2 weeks, a month, or other suitable time periods) (510). Thereafter, a plurality of metrics is generated to define day-to-night change in glucose level for each corresponding day with significant activity (520). With a metric for day-to-night change in glucose level for each day with significant activity and a metric for day-to-night change in glucose level for all days without significant activity, each day metric defining day-to-night change in glucose level for days with significant activity are modified with the metric for day-to-night change in glucose level for days without significant activity (530). Then, a correlation relationship is determined between each modified metric for days with significant activity and the metric for all days without significant activity (540). With the determined correlation, for a given activity level, the impact of the activity level on the overnight glucose level based on the determined correlation is determined and presented to the user (550).

Figure 6:
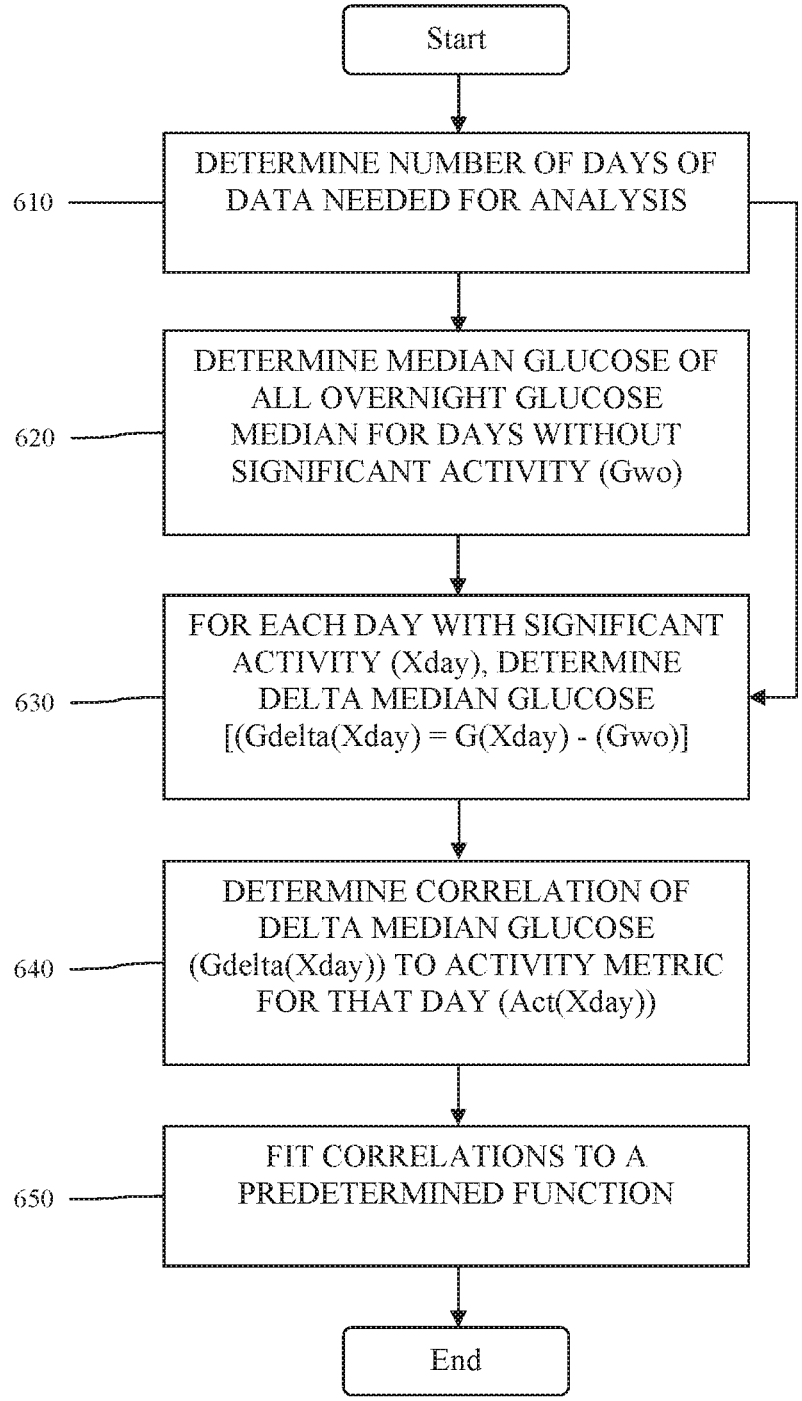
FIG. 6 is a flowchart illustrating glucose response pattern identification and characterization for a particular activity based on absolute overnight glucose level in accordance with one embodiment of the present disclosure.

FIG. 6 is a flowchart illustrating glucose response pattern identification and characterization for a particular activity based on absolute overnight glucose level in accordance with one embodiment of the present disclosure. Referring to FIG. 6, based on the input data received from one or more of the monitors 130A, 130B, 130C, glucose response training unit 112 of analysis module 110B (FIG. 2A) determines whether sufficient amount of data has been received via data input interface 111 (FIG. 2A). In certain embodiments, the amount of data sufficient to perform the glucose response pattern and characterization analysis is based on data received over a predetermined number of days with significant activity, and a predetermined number of days without significant activity (collectively, "X"). In certain embodiments, whether a particular activity qualifies as significant activity is determined based on one or more of activity duration, calories burned during the duration of the activity, the level of intensity of the activity, whether the activity is aerobic or anaerobic activity, or type of activity (for example, competitive activity or non-competitive, training activity). For example, glucose response training unit 112, in certain embodiments, determines that input data from one or more monitors 130A, 130B, 130C (FIG. 1) for 3 days with significant activity and 3 days without significant activity provides the sufficient amount of data for analysis.

In an alternative embodiment, the determination of data sufficiency is based on the degree of certainly of the estimated glycemic pattern, rather than a predetermined number of days of data or amount of data.

Referring to FIG. 6, with the number of days of input data needed for analysis determined (610), glucose response training unit 112 (FIG. 2A) determines median glucose level of all overnight glucose median levels for the determined number of days without significant activity (Gwo) (620). In certain embodiments, number of days without significant activity (Gwo) is defined as the number of days during which the activity measure is below a predefined threshold, such as 10,000 steps during the predetermined day-time period (12 hours, 18 hours, or other suitable time periods). In certain embodiments, the median glucose level of all overnight glucose median levels for the number of days without significant activity (Gwo) varies depending upon the type of activity.

Thereafter, as shown in FIG. 6, for each day with significant activity (Xday), a delta median glucose level (Gdelta (Xday)) is determined (630), where delta median glucose level (Gdelta(Xday)) is the difference between the overnight glucose median for the particular day with significant activity G(Xday) and the median glucose level of all overnight glucose median levels for the determined number of days without significant activity (Gwo). That is:

$$(Gdelta(Xday)) = G(Xday) - (Gwo)$$

In certain embodiments, median glucose level of all overnight glucose median levels for the determined number of days without significant activity (Gwo) (620) and delta median glucose level (Gdelta(Xday)) for each day (630) are simultaneously determined. In other words, steps 620 and 630 can be performed serially, or in parallel relative to each other.

Referring still to FIG. 6, a correlation relationship between the median glucose level for the day (Xday) with significant activity (Gdelta(Xday)) and activity metric (Act (Xday)) for that day is determined (640), and the correlations are fit to a predetermined function (650). In certain embodiments, the correlation relationship includes a linear function, where the delta median glucose level for the days with significant activity (Gdelta(Xday)) is a linear function of the activity metric (Act(Xday)). Within the scope of the present disclosure, the correlation relationship includes a constant offset relationship, an exponential relationship, a logarithmic relationship, or a polynomial relationship, between the delta median glucose level for days with significant activity (Gdelta(Xday)) and the activity metric (Act(Xday)).

Figure 2B:
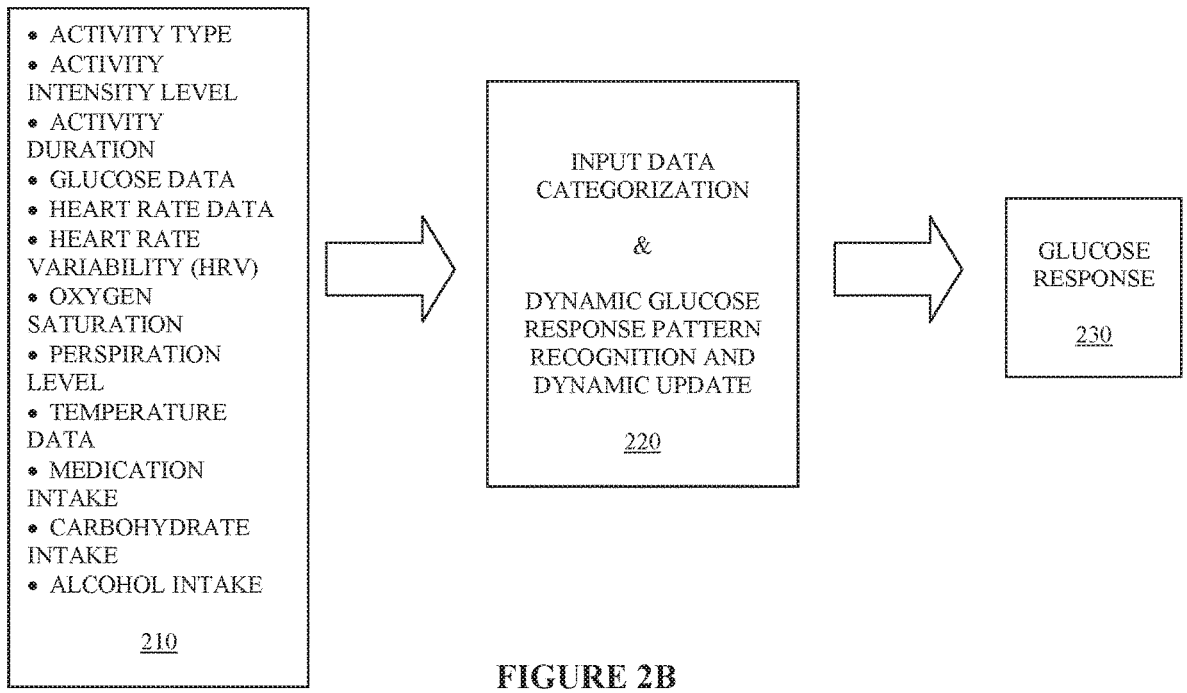
FIG. 2B illustrates the information flow in conjunction with the analysis module of FIG. 1 performing data categorization, pattern recognition and dynamic update in accordance with one embodiment of the present disclosure.

In certain embodiments, activity metric (Act (Xday)) is predetermined for the particular activity that the user or the patient engaged in and is based on, for example, input data categorization 220 (FIG. 2B) performed by glucose response training unit 112 of analysis module 110B. (FIG. 2A). In certain embodiments, activity metric (Act (Xday)) varies depending on one or more parameters associated with the activity including, for example, activity duration, intensity level, activity type, heart rate data associated with the activity, among others. In certain embodiments, the activity metric (Act(Xday)) includes a "step-rate" such as steps-per-hour, or steps over a predetermined or fixed time duration.

In certain embodiments, least squares technique is applied to fit the correlation relationship to the data set. For example, least squares approach can be applied to the data set to determine the slope and offset for the linear relationship defining the correlation between the delta median glucose level for days with significant activity (Gdelta(Xday)) and the activity metric (Act(Xday)). In certain embodiments, the linear relationship is subsequently applied by the App to predict or anticipate the impact of significant exercise on over-night glucose levels. In other words, with a known or determined activity metric (Act(Xday)), the App estimates the resulting delta median glucose level for days with significant activity (Gdelta(Xday)) by multiplying the activity metric (Act(Xday)) by the slope of the linear correlation relationship and adding the offset, where the slope and offset are parameters determined by a best fit analysis, for example. In certain embodiments, the best fit analysis is updated with each revision or addition of the data set collected or received from monitors (130A-130C FIG. 1). Alternatively, in certain embodiments, the best fit analysis is updated after a predetermined time period of data set collection.

In certain embodiments, a set of ratios (R) determined for each day with significant activity is determined. The ratios are calculated as the delta median glucose level for days with significant activity (Gdelta(Xday)) divided by the activity metric (Act(Xday)). The median or mean of the set of ratios are then calculated. The impact of the activity is then determined by multiplying the median of the set of ratios (R) times the current activity metric (Act(Xday)). Alternatively, within the scope of the present disclosure, curve fitting approach is applied such as using least squares technique to fit the set of ratios (R's) to a least squares fit line, for example.

Referring back to FIG. 6, in certain embodiments, the number of days needed for analysis (610) can be determined by the quality of the correlation (650). For example, in certain embodiments, linear line fit analysis provides metrics that indicate the quality of such line fit (for example, correlation coefficient ($R^2$) or standard error of the delta median glucose level for days with significant activity (Gdelta(Xday)) estimate). The data set, in certain embodiments, is determined to be sufficient (610) if the line fit quality metric exceeds a specific value, for example (but not limited to) when the $R^2$ value is greater than 0.9, or the standard error of the delta median glucose level for days with significant activity (Gdelta(Xday)) for the line fit is less than 10%. If the line fit is determined to be invalid, in certain embodiments, the App is configured to continue with analysis of the data set (i.e., continue training), and each day the line fit is updated to determine if it is valid. When the line fit is determined to be valid, then the analysis result, in certain embodiments, is presented to the user, for example, at the data output interface 113 of analysis module 110B (FIG. 2A).

By way of a nonlimiting example, Table 1 below illustrates data set collected for glucose response pattern identification and characterization using number of steps taken as activity in accordance with certain embodiments of the present disclosure.

TABLE 1

14 days of activity vs nonactivity data

| Day | Activity? | Activity Metric (steps) | Daytime Median Glucose (mg/dL) | Overnight Median Glucose (mg/dL) |
|---|---|---|---|---|
| 1 | yes | 12503 | 143 | 117 |
| 2 | no | 3043 | 156 | 142 |
| 3 | no | 2043 | 142 | 150 |
| 4 | yes | 11432 | 150 | 125 |
| 5 | yes | 16490 | 146 | 111 |
| 6 | yes | 13083 | 151 | 120 |
| 7 | no | 1044 | 143 | 160 |
| 8 | no | 1453 | 145 | 151 |
| 9 | yes | 10984 | 149 | 131 |
| 10 | no | 2354 | 139 | 140 |
| 11 | no | 2356 | 161 | 139 |
| 12 | no | 1234 | 155 | 144 |
| 13 | yes | 19245 | 144 | 105 |
| 14 | no | 7034 | 147 | 143 |

From Table 1 above, it can be seen that over the two week period, there were 6 days with activity (determined as number of steps exceeding a threshold level—e.g., 10000 steps taken within a 24 hour period) including days 1, 4, 5, 6, 9, and 13. It can also be seen that during the two week period, there were 8 days without activity (determined as the number of steps below the threshold level of 10000 steps within a 24 hour period) including days 2, 3, 7, 8, 10, 11, and 12.

Given the daytime median glucose level for each of the 14 days and also the corresponding overnight median glucose level for each of the 14 days, the median glucose level of all overnight median glucose level for days without significant activity (Gwo) is determined by taking the median of the overnight median glucose level of days 2, 3, 7, 8, 10, 11, and 12 from Table 1, which is 143.5 mg/dL. Further, for each day with activity (e.g., days 1, 4, 5, 6, 9, and 13), the delta median glucose (Gdelta(Xday)) is determined by subtracting median glucose level of all overnight median glucose level for days without significant activity (Gwo) determined as 143.5 mg/dL from the corresponding overnight median glucose level (G(Xday)). For example, for day 1 (activity), the delta median glucose (Gdelta(day1)) is 117 mg/dL subtracted by 143.5 mg/dL (median glucose level of all overnight median glucose level for days without significant activity (Gwo)) results is the delta median glucose (Gdelta(day1)) of −26.5. Similarly, for day 4 (activity), the delta median glucose (Gdelta(day4)) is −18.5 (125 mg/dL subtracted by 143.5 mg/dL). For day 5 (activity), the delta median glucose (Gdelta(day5)) is −32.5 (111 mg/dL subtracted by 143.5 mg/dL). For day 6 (activity), the delta median glucose (Gdelta(day6)) is −23.5 (120 mg/dL subtracted by 143.5 mg/dL). For day 9 (activity), the delta median glucose (Gdelta(day9)) is −12.5 (131 mg/dL subtracted by 143.5 mg/dL). Finally, for day 13 (activity), the delta median glucose (Gdelta(day13)) is −38.5 (105 mg/dL subtracted by 143.5 mg/dL).

With the delta median glucose for each day with activity (Gdelta(Xday)) determined as described above, a corresponding R value for each day with activity is determined by dividing the determined delta median glucose (Gdelta(Xday)) with the activity metric (Act(Xday)) for the corresponding day with activity. For example, R value for day 1 is −0.002 (−26.5 divided by 12,503 steps (activity metric for day 1). In this manner, the R value for the days with activity is determined and the resulting values are shown as below in Table 2 (with the corresponding delta median glucose level (Gdelta(Xday)).

TABLE 2

| Day | Activity? | Activity Metric (steps) | Overnight Median Glucose (mg/dL) | Delta Median Glucose (Gdelta) | R |
|---|---|---|---|---|---|
| 1 | yes | 12503 | 117 | −26.5 | −0.002119491 |
| 4 | yes | 11432 | 125 | −18.5 | −0.001618265 |
| 5 | yes | 16490 | 111 | −32.5 | −0.001970891 |
| 6 | yes | 13083 | 120 | −23.5 | −0.001796224 |
| 9 | yes | 10984 | 129 | −14.5 | −0.001320102 |
| 13 | yes | 19245 | 105 | −38.5 | −0.00200052 |

Figure 11:
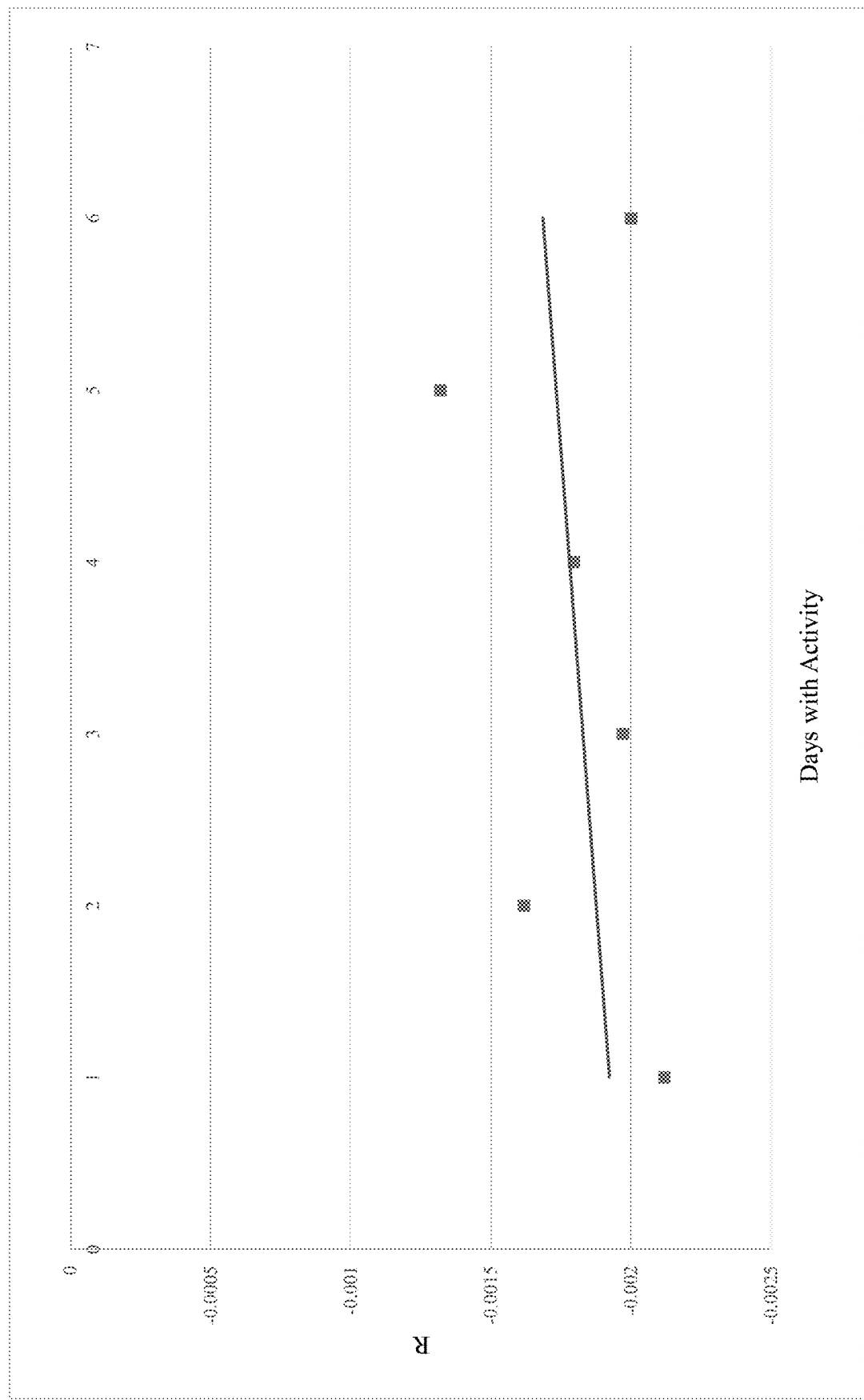
FIG. 11 is a graph of an exemplary line fit analysis in accordance with the one embodiment of the present disclosure.

Based on the data set determined as shown in Table 2 above, a line fit analysis is performed on the days with activity against the corresponding R values as shown in FIG. 11.

Alternatively, the median or mean of the R values can be used to represent the glycemic pattern. Further, a line fit analysis can be performed on the delta median glucose (Gdelta(Xday)) with respect to the activity level (number of steps) and as shown in FIG. 12 where it can be seen that the correlation value ($R^2$) is 0.9125 demonstrating acceptable correlation, and where the line fit analysis provides an offset of 10.811 with a slope of −0.0026, This line represents the glycemic pattern.

Figure 12:
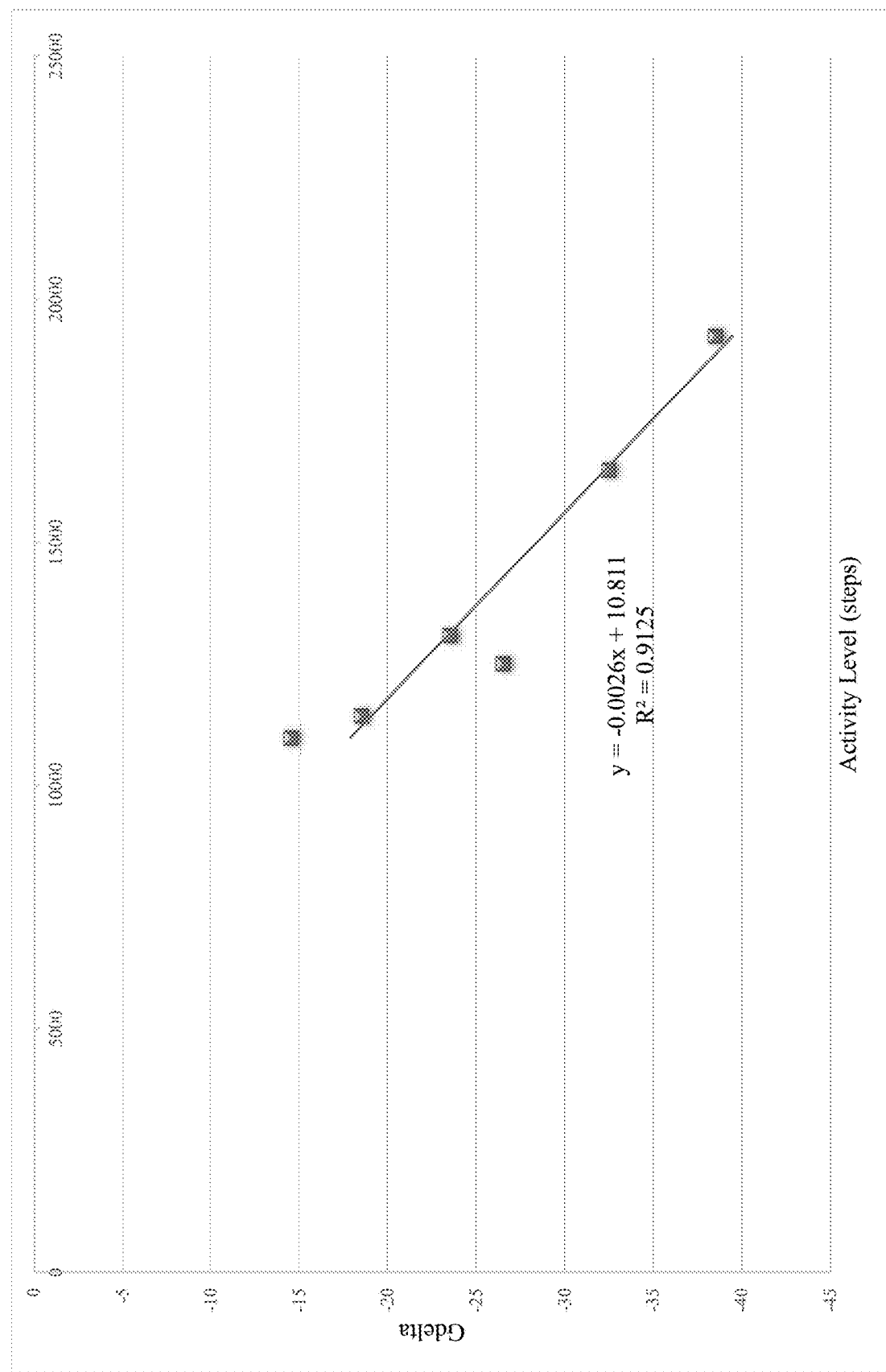
FIG. 12 is a graph of an exemplary line fit analysis in accordance with the one embodiment of the present disclosure.

Using FIG. 12, when the user decides to perform a particular activity that will result in 15,000 steps, from the line fit analysis, it can be seen that such activity will result in a reduction of the glucose level by approximately 28 mg/dL. With this information, if the user desires to maintain a tighter glycemic control, and knowing that performing 15,000 steps will reduce the glucose level by approximately 28 mg/dL, the user can take proactive actions to counter the effects of the activity (e.g., 15,000 step) by, for example, consuming more food and/or drinks either before or during engaging in the activity.

In an alternate embodiment, the activity metric is transformed into two values: significant activity or not significant activity. In this case, an overnight glucose median level is associated with either a day of significant activity or with a day without, where significant activity is defined as when the activity measure exceeds a predefined threshold (for example, the number of steps exceeding 10,000 steps for the day). More specifically, referring to Table 1, the median glucose for all overnight periods associated with days of significant activity are determined (days 1, 4, 5, 6, 9, and 13) as 118.5 mg/dL, as well as the median glucose level for all overnight periods associated with non-significant activity (days 2, 3, 7, 8, 10, 11, 12, and 14) as 143.5 mg/dL. Then, the decrease in median activity is determined by subtracting 143.5 mg/dL (as the median glucose level for all overnight periods associated with nonsignificant activity) from 118.5 mg/dL (the median glucose for all overnight periods associated with days of significant activity), which results in −25 mg/dL. The percentage median decrease is then 17.42% (−25 mg/dL divided by 143.5 mg/dL). In this approach, whether sufficient number of days of data set has been collected can be determined by using standard statistical tests for determining if the means of two different populations are different. For example, by confirming that the standard deviation of each median overnight glucose determination (with and without activity) is below a predefined threshold, such as 20 mg/dL, for example. Referring to Table 1, the standard deviation for days with significant activity (days 1, 4, 5, 6, 9, and 13) is 8.864 mg/dL, while the standard deviation for days without significant activity (days 2, 3, 7, 8, 10, 11, 12, and 14) is 7.08 mg/dL.

Referring again to the Figures, with the glucose response pattern identification and characterization described above, the App, in certain embodiment, is configured to output to the user when subsequent significant activity is detected: "For days with significant activity, overnight glucose levels tend to be 25 mg/dL lower, than for days without significant activity." Alternatively, this result may be displayed as a percentage, for this example, 17% lower. Within the scope of the present disclosure, the technique described above can be expanded to any level of quantization such as three or four levels.

In certain embodiments, using the routine described above in conjunction with FIG. 6, glucose response training unit 112 of analysis module 110B (FIG. 2A) identifies consistent glucose response to a particular activity with specific parameters. The user or the patient then uses this information to modify or adjust therapy protocol, meals consumed or the type of activity to engage in given the underlying physiological state, to maintain tight glycemic control and improve health condition.

Figure 7:
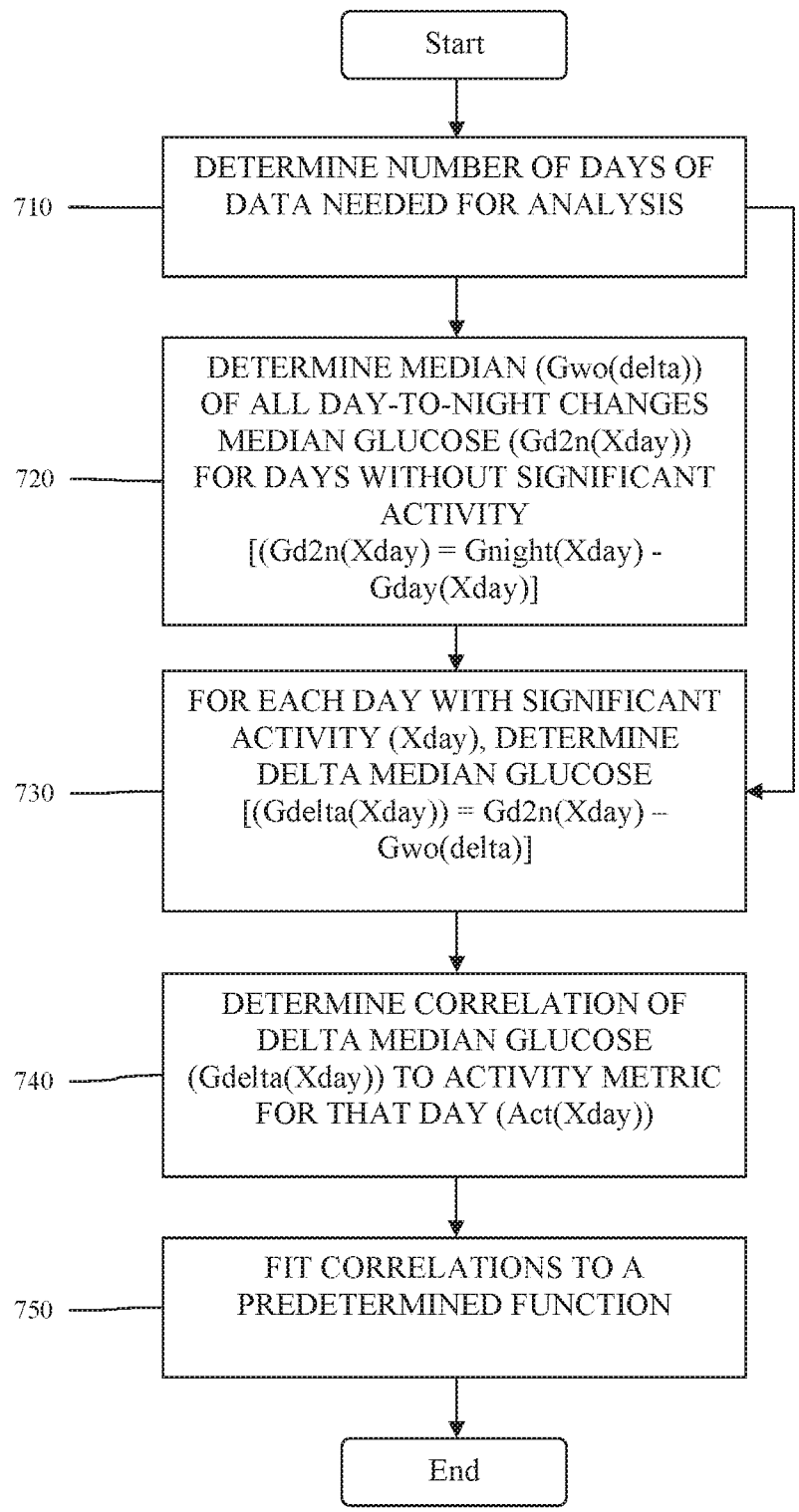
FIG. 7 is a flowchart illustrating glucose response pattern identification and characterization for a particular activity based on day-to-night glucose level change in accordance with one embodiment of the present disclosure.

FIG. 7 is a flowchart illustrating glucose response pattern identification and characterization for a particular activity based on day-to-night glucose level change in accordance with one embodiment of the present disclosure. Referring to FIG. 7, similar to step 510 of FIG. 5, based on the input data received from one or more of the monitors 130A, 130B, 130C, glucose response training unit 112 of analysis module 110B (FIG. 2A), determines whether sufficient amount of data has been received via data input interface 111 (FIG. 2A) (710). Then, glucose response training unit 112 of analysis module 110B determines median (Gwo(delta)) of all day-to-night changes in glucose median (Gd2n(Xday)) for days (in the number of days determined to provide sufficient amount of data) without significant activity (720).

More specifically, each day-to-night changes in glucose median without significant activity (Gd2n(Xday)) is determined by subtracting the median glucose level over a first predetermined time-of-day period (e.g., from 8 am to 10 pm) (Gday(Xday)) from the median glucose level over a second predetermined time-of-day period (e.g., from 10 am to 6 pm) (Gnight(Xday)) (720). That is:

$$(Gd2n(Xday)) = Gnight(Xday) - Gday(Xday)$$

Within the scope of the present disclosure the time periods and ranges for the first and second predetermined time-of-day periods may be varied so that one is longer than the other, or alternatively, the two periods are the same length. In certain embodiments, the first and second predetermined time periods for each day are determined based on specific events such as meal events or other indicators associated with the patient.

Referring back to FIG. 7, with the median of all day-to-night changes in median glucose for days without significant activity (Gwo(delta)) determined (720), glucose response training unit 112, in certain embodiments, determines delta median glucose level (Gdelta(Xday)) by subtracting median of all day-to-night changes in glucose median for days without significant activity (Gwo(delta)) from the day-to-night changes in glucose median without significant activity (Gd2n(Xday)) (730). In certain embodiments, determination of median of all day-to-night changes in median glucose for days without significant activity (Gwo(delta)) (720) and the delta median glucose level (Gdelta(Xday)) for each day with significant activity (730) are determined simultaneously rather than in sequence. In alternate embodiments, the delta median glucose level (Gdelta(Xday)) for each day with significant activity (730) may be determined before median of all day-to-night changes in median glucose for days without significant activity (Gwo(delta)) (720).

Thereafter, a correlation relationship is determined between delta median glucose (Gdelta(Xday)) and activity metric (Act (Xday)) for each day with significant activity (Xday) (740). Similar to the routine performed in conjunction with FIG. 6, in certain embodiments, activity metric (Act (Xday)) is predetermined for the particular activity that the user or the patient engaged in, and as such may be based on input data categorization (FIG. 2B) performed by glucose response training unit 112 of analysis module 110B. (FIG. 2A). Similarly, in certain embodiments, activity metric (Act (Xday)) varies depending on one or more parameters associated with the activity including, for example, activity duration, intensity level, activity type, heart rate data associated with the activity.

Again, similar to the routine executed in conjunction with FIG. 6, referring to FIG. 7, once the correlation relationship between the delta median glucose level for the day (Xday) with significant activity (Gdelta(Xday)) and activity metric (Act (Xday)) for that day is determined (740), the correlation relationship, for instance, where the delta median glucose level for days with significant activity (Gdelta(Xday)) is represented as a linear function of the activity metric (Act (Xday)), is used to generate an estimate of the delta median glucose level for days with significant activity (Gdelta (Xday)) of the next overnight period for days of significant activity, and the analysis result are displayed to the user. That is, the correlations are fit to a predetermined function (750) and the resulting relationship is output to the user.

For example, referring to the data set shown in Table 1, the median of all day-to-night changes in glucose median for days without significant activity (Gwo(delta)) is −1.5. This is derived from determining the median of all day-to-night changes in glucose median without significant activity (Gd2n(Xday)). That is, from Table 1, for each day without significant activity (days 2, 3, 7, 8, 10, 11, 12, and 14), the median day-to-night changes in glucose median (Gd2n (Xday)) is determined by subtracting the daytime median glucose level from the overnight glucose level. For example, the median of day-to-night changes in glucose median for day 2 (Gd2n(day2)) is −14 mg/dL (142 mg/dL-156 mg/dL). The median of day-to-night changes in glucose median for day 3 (Gd2n(day3)) is 8 mg/dL (150 mg/dL-142 mg/dL). The median of day-to-night changes in glucose median for day 7 (Gd2n(day7)) is 17 mg/dL (160 mg/dL-143 mg/dL). The median of day-to-night changes in glucose median for day 8 (Gd2n(day8)) is 6 mg/dL (151 mg/dL-145 mg/dL). The median of day-to-night changes in glucose median for day 10 (Gd2n(day10)) is 1 mg/dL (140 mg/dL-139 mg/dL). The median of day-to-night changes in glucose median for day 11 (Gd2n(day11)) is −22 mg/dL (139 mg/dL-161 mg/dL). The median of day-to-night changes in glucose median for day 12 (Gd2n(day12)) is −11 mg/dL (144 mg/dL-155 mg/dL). Finally, the median day-to-night changes in glucose median for day 14 (Gd2n(day14)) is −4 mg/dL (143 mg/dL-147 mg/dL). This is illustrated in Table 3 below.

TABLE 3

| Day | Activity? | Activity Metric (steps) | Daytime Median Glucose (mg/dL) | Overnight Median Glucose (mg/dL) | Median day-to-night glucose change Gd2n | Median of all day-to-night changes in glucose median for days without significant activity Gwo (delta) |
|---|---|---|---|---|---|---|
| 2 | no | 3043 | 156 | 142 | −14 | |
| 3 | no | 2043 | 142 | 150 | 8 | |
| 7 | no | 1044 | 143 | 160 | 17 | |
| 8 | no | 1453 | 145 | 151 | 6 | |
| 10 | no | 2354 | 139 | 140 | 1 | |
| 11 | no | 2356 | 161 | 139 | −22 | |
| 12 | no | 1234 | 155 | 144 | −11 | |
| 14 | no | 7034 | 147 | 143 | −4 | −1.5 |

With the median of all day-to-night changes in glucose median for days without significant activity (Gwo(delta)) determined as −1.5, for each day with significant activity, the delta median glucose (Gdelta(Xday)) can be determined by subtracting the median day-to-night changes in glucose median for each day by the median of all day-to-night changes in glucose median for days without significant activity (Gwo(delta)). This is shown in table 4 below.

TABLE 4

| Day | Activity? | Activity Metric (steps) | Daytime Median Glucose (mg/dL) | Overnight Median Glucose (mg/dL) | Median day-to-night glucose change Gd2n | Delta Median Glucose Gdelta | R |
|---|---|---|---|---|---|---|---|
| 1 | yes | 12503 | 143 | 117 | −26 | −24.5 | −0.00195953 |
| 4 | yes | 11432 | 150 | 125 | −25 | −23.5 | −0.002055633 |
| 5 | yes | 16490 | 146 | 111 | −35 | −33.5 | −0.002031534 |
| 6 | yes | 13083 | 151 | 120 | −31 | −29.5 | −0.002254835 |
| 9 | yes | 10984 | 149 | 131 | −18 | −16.5 | −0.001502185 |
| 13 | yes | 19245 | 144 | 105 | −39 | −37.5 | −0.001948558 |

As can be seen from Table 4, for each day with significant activity, a corresponding R value is determined by dividing the determined delta median glucose (Gdelta(Xday)) with the activity metric (Act(Xday)) for the corresponding day with activity.

In addition, in certain embodiments, rather than a linear function, a set of ratios (R) determined for each day with significant activity is generated. The ratios R are determined by dividing delta median glucose (Gdelta(Xday)) for each day with significant activity by the corresponding activity metric (Act(Xday)). The median or mean of the set of ratios R is then determined (in this case, the median of the R values for days with significant activity is −0.00199553198802936). The effect of activity can then be determined by multiplying the median R by the current activity metric (Act(Xday)). Alternatively, curve fitting techniques can be applied using, for example, least squares to fit the set of ratios (R's) to a line.

Figure 13:
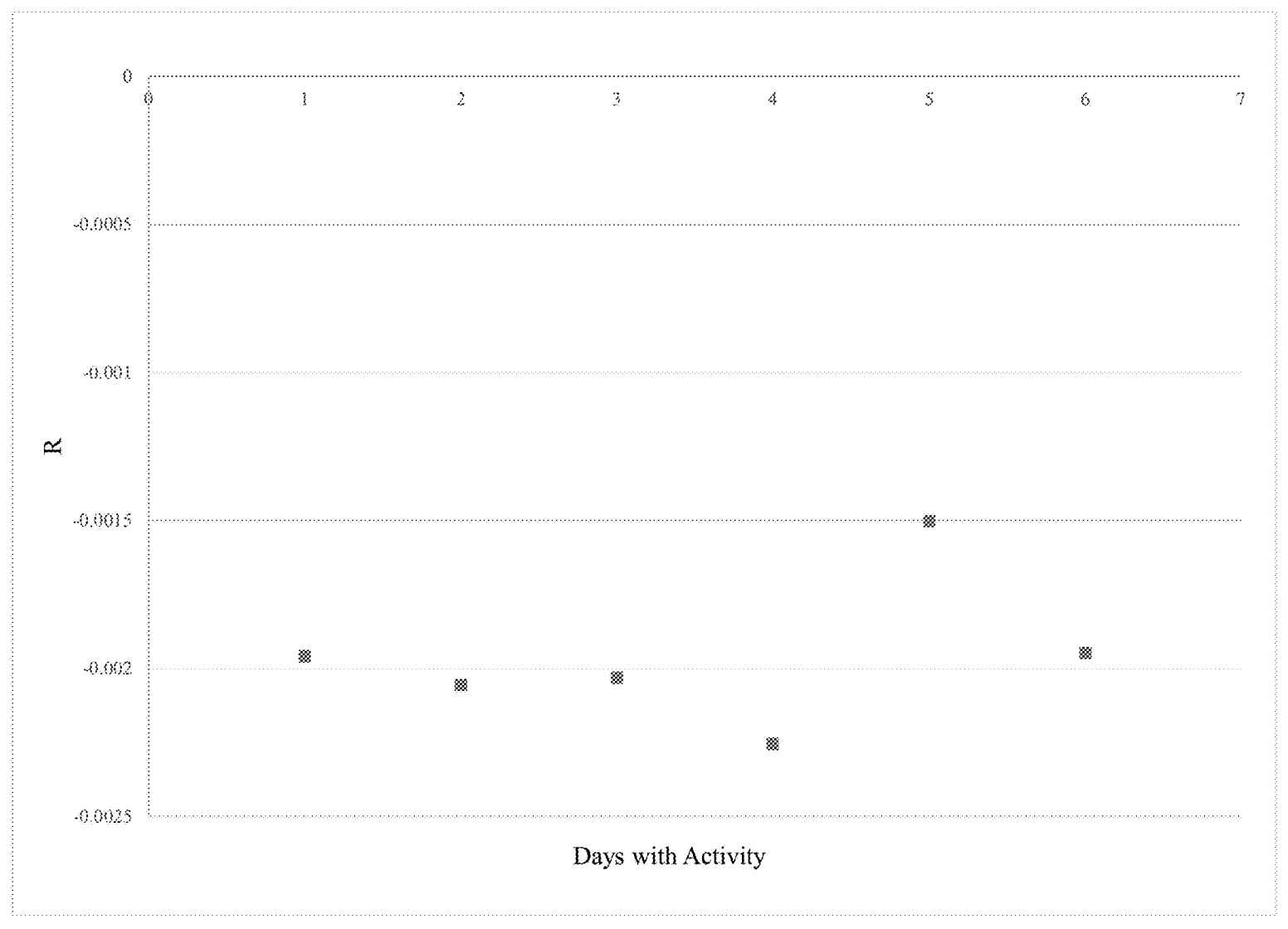

FIG. 13 shows the R values plotted against the days with activity.

Alternatively, the median or mean of the R values can be used to represent the glycemic pattern. Further, the delta median glucose (Gdelta(Xday)) can be plotted against the activity metric (Act(Xday)) and a line fit analysis performed, resulting in the plot shown in FIG. 14.

Figure 14:
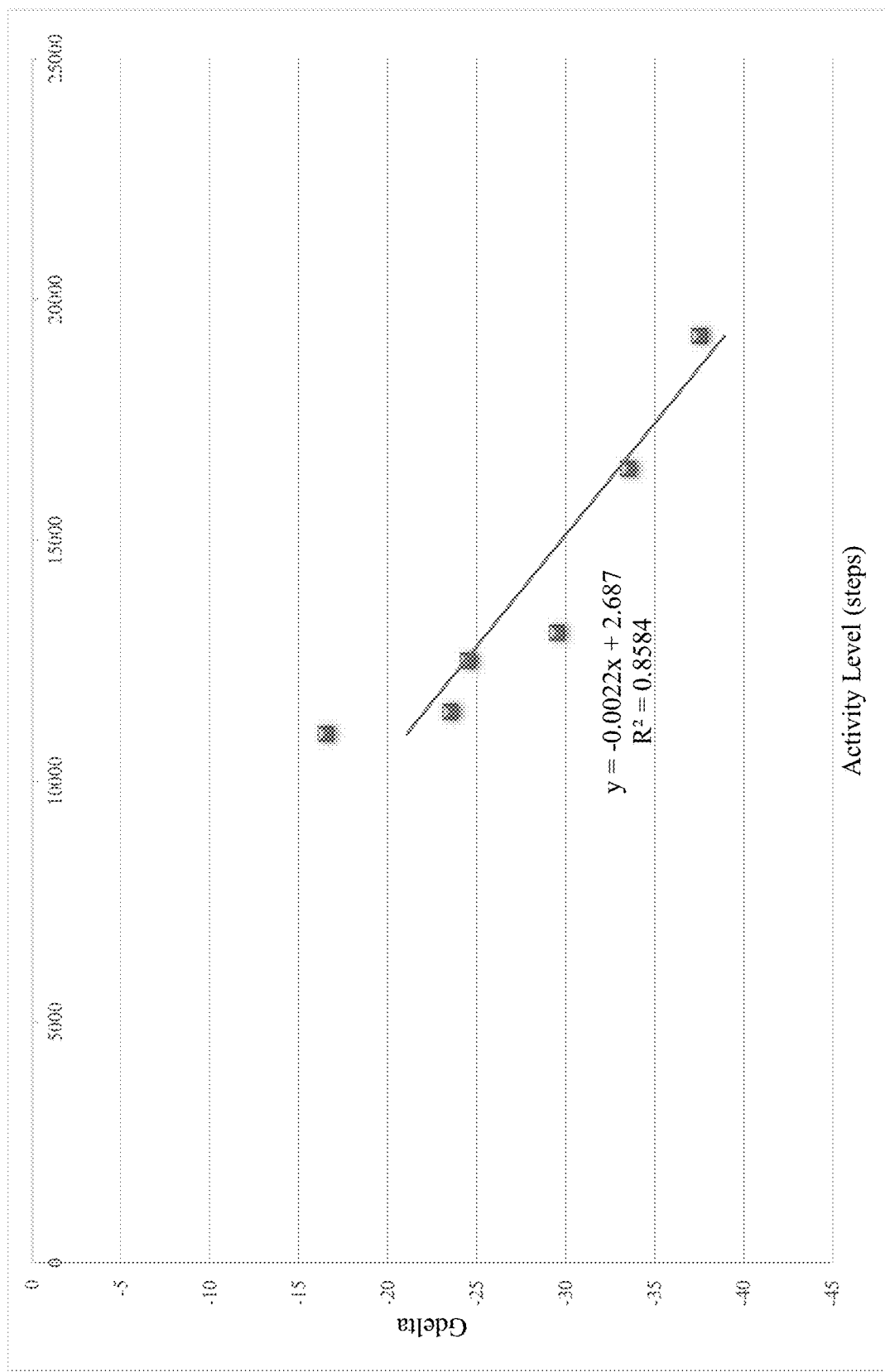
FIG. 14 is a graph of an exemplary line fit analysis in accordance with the one embodiment of the present disclosure.

From the line fit analysis shown in FIG. 14, the correlation coefficient $R^2$ is approximately 0.86, with an offset of 2.687 for the line fit, and a slope of −0.0022. With the analysis shown in FIG. 14, a user who wishes to engage in an activity that includes 15,000 steps, can ascertain from FIG. 14 that such activity will result in a glucose level reduction of approximately 30 mg/dL. Alternatively, the App includes a routine that estimates the upcoming overnight Gdelta(Xday) by inputting the day's activity into the linear equation. The user can then decide to take appropriate action (consume additional food/drink during or pre-activity) to better control the anticipated glucose level drop resulting from the activity.

In an alternate embodiment, the activity metric (Act(Xday)) can be categorized into two values: significant activity or not significant activity. In such a case, an overnight glucose median is associated with either a day of significant activity or with a day without significant activity, where significant activity is determined if the activity measure exceeds a predefined threshold (for example, greater than 10,000 steps for a day time period). The median day-to-night changes in median glucose level (Gd2n(Xday)) for all overnight periods associated with days with significant activity are determined, as well as the median day-to-night changes in median glucose level (Gd2n(Xday)) for all overnight periods associated with non-significant activity, and the decrease in median activity is then determined. Data sufficiency, in certain embodiments, are determined using statistical techniques; for example, by verifying that the standard error of each median calculation is below a predefined threshold, such as 20 mg/dL.

For example, the median day-to-night changes in median glucose level (Gd2n(Xday)) for all overnight periods associated with days with significant activity is determined as −28.5 mg/dL (taking the median of day-to-night changes in median glucose level for days 1, 4, 5, 6, 9, and 13—which are −26, −25, −35, −31, −18, and −39, respectively), while the median day-to-night changes in median glucose level (Gd2n(Xday)) for all overnight periods associated with non-significant activity is determined as −1.5 mg/dL (taking the median of the day-to-night changes in median glucose level for days 2, 3, 7, 8, 10, 11, 12, and 14—which are −14, 8, 17, 6, 1, −22, −11, and −4, respectively). From this, the median decrease in glucose level can be determined as −27 mg/dL (subtracting −1.5 mg/dL from −28.5 mg/dL).

In this case, the analysis result is displayed by the App to the user when subsequent significant activity is detected as follows: "For days with significant activity, glucose levels tend to be 27 mg/dL lower than for days without significant activity." Within the scope of the present disclosure, the analysis can be expanded to any level of quantization such as three or four levels.

Figure 8:
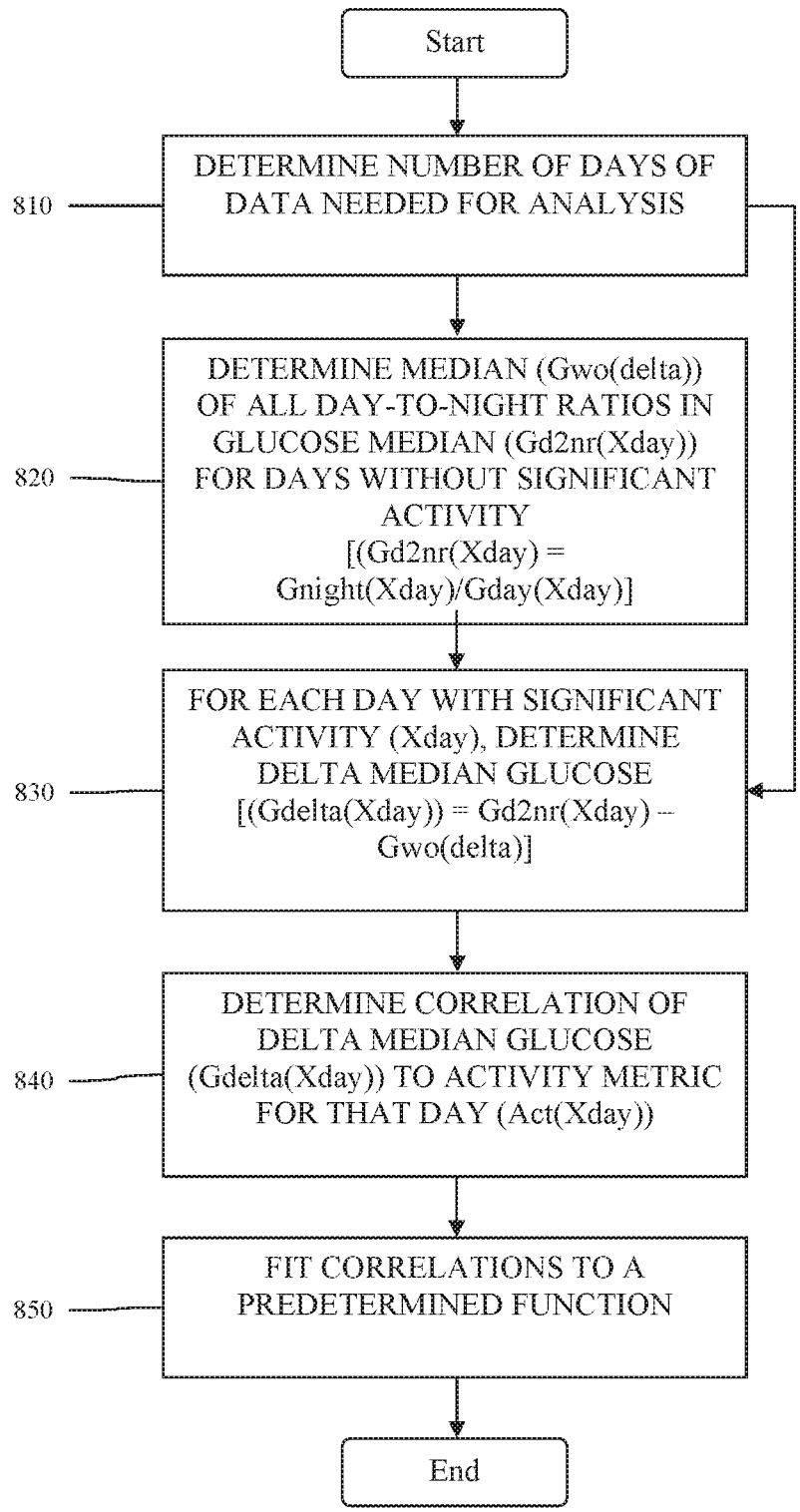
FIG. 8 is a flowchart illustrating glucose response pattern identification and characterization for a particular activity based on day-to-night glucose level ratio in accordance with one embodiment of the present disclosure.

FIG. 8 is a flowchart illustrating glucose response pattern identification and characterization for a particular activity based on day-to-night glucose level ratio in accordance with one embodiment of the present disclosure. Referring to FIG. 8, the difference between the routine executed by glucose response training unit 112 of analysis module 110B (FIG. 2A) in conjunction with FIG. 7 compared to the routine shown in FIG. 8 is that instead of using the median (Gwo(delta)) of all day-to-night changes in glucose median level (Gd2n(Xday)) for days without significant activity (at step 720 in FIG. 7, the routine in FIG. 8 determines median (Gwod2nr) of all day-to-night ratios in glucose median level (Gd2nr(Xday)) for days without significant activity (820) after the number of days of data needed for analysis is determined (810). In certain embodiments, the day-to-night ratios in glucose median level (Gd2nr(Xday)) for days without significant activity is determined by dividing the median glucose level over a second predetermined time-of-day period (e.g., from 10 pm to 6 am) (Gnight(Xday)) by median glucose level over a first predetermined time-of-day period (e.g., from 8 am to 10 pm) (Gday(Xday)). That is:

$$(Gd2nr(Xday)) = Gnight(Xday)/Gday(Xday)$$

Referring back to FIG. 8, the median (Gwo(delta)) of all day-to-night ratios in glucose median level (Gd2nr(Xday)) for days without significant activity is determined. The glucose response training unit 112 of analysis module 110B then determines, for each day with significant activity, the delta median glucose (Gdelta(Xday)) by subtracting each of the day-to-night ratios (Gd2nr(Xday)) for each day with significant activity (830) by the median (Gwo(delta)) of all day-to-night ratios in glucose median level for days without significant activity. In certain embodiments, after determining the number of days of data needed for analysis (810), the median (Gwo(delta)) of all day-to-night ratios in glucose median (Gd2nr(Xday)) for days without significant activity (820), and the delta median glucose (Gdelta(Xday)) for each day with significant activity (830) are simultaneously determined rather than sequentially.

Referring again to FIG. 8, similar to FIG. 7 step 740, the correlation relationship between the delta median glucose (Gdelta(Xday)) and activity metric (Act (Xday)) for each day is determined (840). This correlation relationship indicates the proportional decrease in the ratio of day-to-night glucose levels overnight after significant activity. The correlation of delta median glucose (Gdelta(Xday)) to activity metric (Act(Xday)) for the days with significant activity are fit to a predetermined function (850), and the resulting correlation information output to the user.

Referring again to the data set shown in Table 1 above, the analysis described in conjunction with FIG. 8 results in median of all day-to-night ratios in glucose median level (Gwod2nr) as 0.989991680125287, based on the median of the day-tonight ratio in glucose median level of days without significant activity as shown in Table 5 below:

TABLE 5

| Day | Activity? | Activity Metric (steps) | Daytime Median Glucose (mg/dL) | Overnight Median Glucose (mg/dL) | day-to-night ratios in glucose median Gd2nr | Median of all day-to-night ratios in glucose median without significant activity Gwod2nr |
|---|---|---|---|---|---|---|
| 2 | no | 3043 | 156 | 142 | 0.91 | |
| 3 | no | 2043 | 142 | 150 | 1.056 | |
| 7 | no | 1044 | 143 | 160 | 1.119 | |
| 8 | no | 1453 | 145 | 151 | 1.041 | |
| 10 | no | 2354 | 139 | 140 | 1.007 | |
| 11 | no | 2356 | 161 | 139 | 0.863 | |
| 12 | no | 1234 | 155 | 144 | 0.929 | |
| 14 | no | 7034 | 147 | 143 | 0.973 | 0.98999168 |

Then, the ratio of median level glucose (Gactd2nr(Xday)) for each day with significant activity can be determined by dividing the median of each day-to-night ratios in glucose median level (Gwod2nr) of 0.989991680125287 from the day-to-night ratios in glucose median (Gactd2nr(Xday)) for each day with significant activity as shown below in Table 6.

TABLE 6

| Day | Activity? | Activity Metric (steps) | Daytime Median Glucose (mg/dL) | Overnight Median Glucose (mg/dL) | Day-to-night ratios in glucose median with significant activity Gd2nr | Ratio of median glucose Gactd2nr |
|---|---|---|---|---|---|---|
| 1 | yes | 12503 | 143 | 117 | 0.818 | 0.82645323 |
| 4 | yes | 11432 | 150 | 125 | 0.833 | 0.84175792 |
| 5 | yes | 16490 | 146 | 111 | 0.76 | 0.76795996 |
| 6 | yes | 13083 | 151 | 120 | 0.795 | 0.80273603 |
| 9 | yes | 10984 | 149 | 131 | 0.879 | 0.88808285 |
| 13 | yes | 19245 | 144 | 105 | 0.729 | 0.73653818 |

From Table 6, the median of the median glucose ratios (Gactd2nr(Xday)) for days with significant activity can be determined as 0.814595. Alternatively, a line fit analysis can be performed by plotting the median glucose ratio (Gactd2nr (Xday)) against the activity metric (Act) for days with significant activity as shown in FIG. 15.

Figure 15:
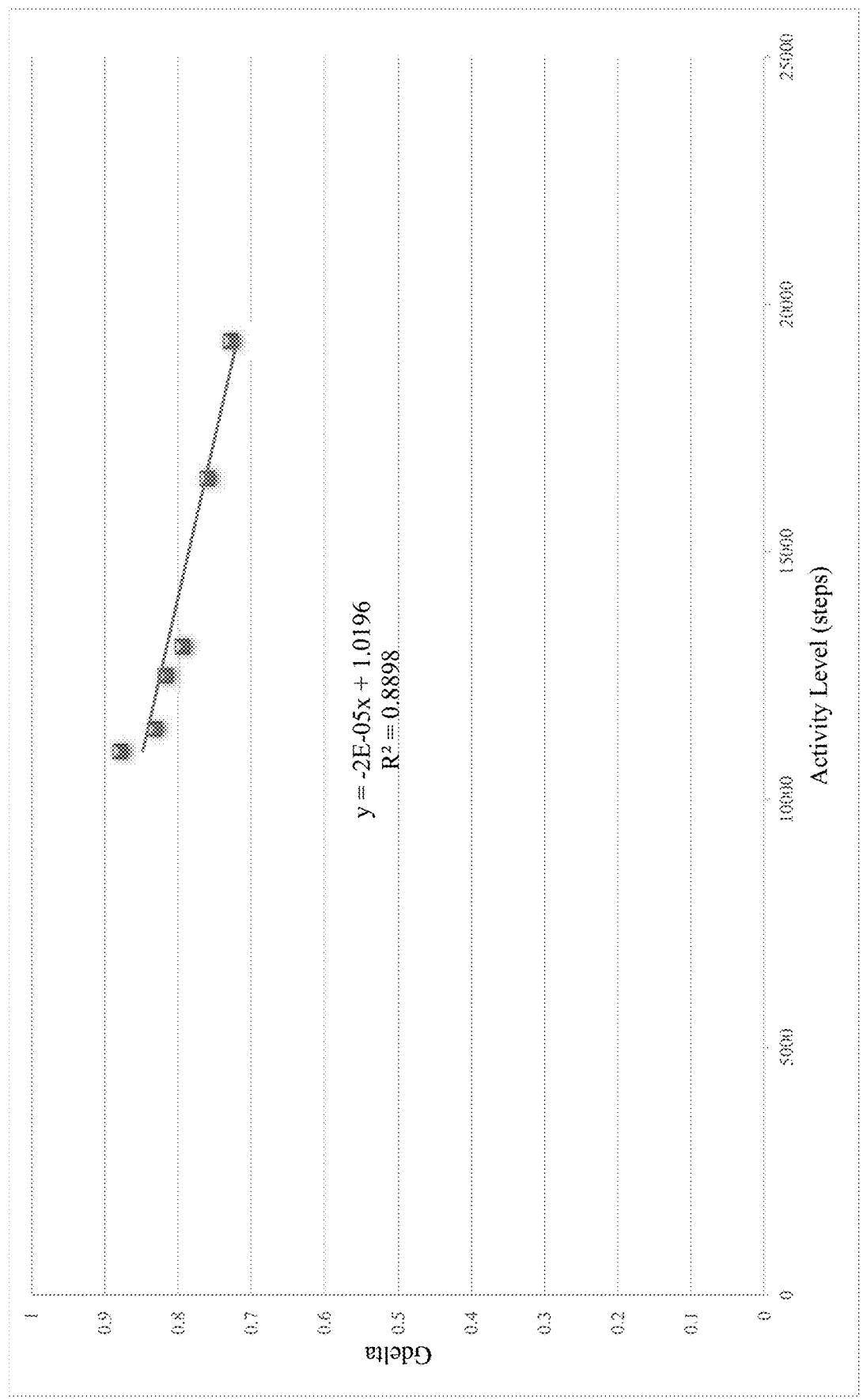
FIG. 15 is a graph of an exemplary line fit analysis in accordance with the one embodiment of the present disclosure.

It can be seen that the correlation coefficient R2 from FIG. 15 is approximately 0.89, with an offset of approximately 1.03 and a slope of −0.00002(2E-05).

Figure 9:
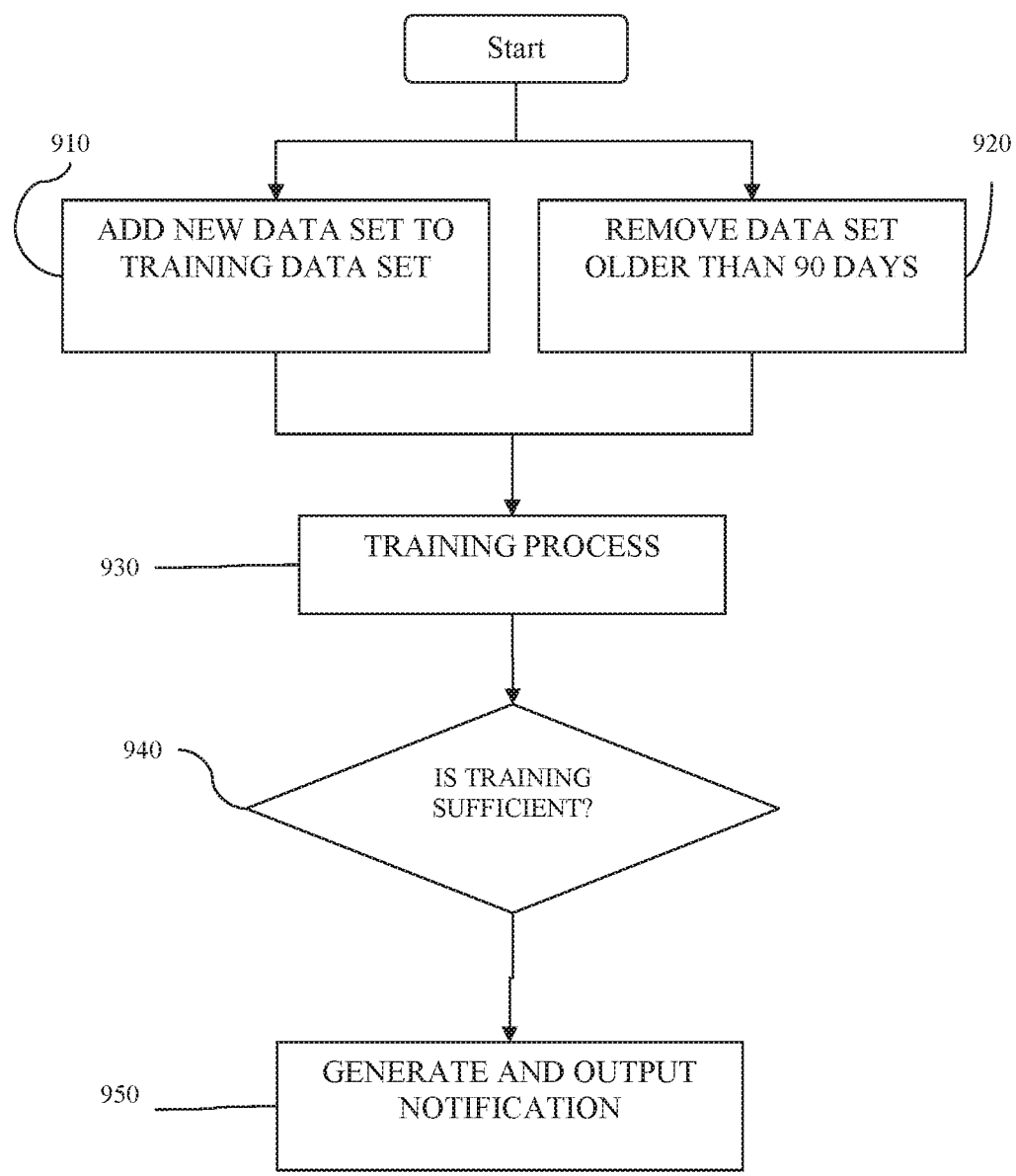
FIG. 9 illustrates a process flow for training and notification in accordance with one embodiment of the present disclosure.

FIG. 9 illustrates a process flow for training and notification in accordance with one embodiment of the present disclosure. Referring to FIG. 9, in certain embodiments, data analysis training for example, described in conjunction with FIGS. 4-8 above, are performed on input data set received (910), at a predetermined time interval such as once daily. Every time the routine is executed, new data set that has been acquired is added to the data set maintained and used for data analysis training, for example, to determine the correlation relationship between activity and future glucose levels (e.g., overnight glucose level).

Referring back to FIG. 9, in addition to adding new data set to the training data set (910), each time the data analysis training routine is executed, older data is removed from the training set, such as data that is 90 days or older or 180 days or older or any other suitable time periods (920). This allows the data analysis training routine to adapt to the changing physiology of the user from whom the data set is derived ("forgetting"). In certain embodiments, the "forgetting" subroutine may be excluded or optional. When the data analysis training process has concluded (930), training sufficiency is checked (940) as described above in conjunction with FIG. 48 such that, for example, the uncertainty metric associated with the "fit" of the correlation relationship is less than a predetermined threshold. If it is determined that that training is sufficient (940), then notification of the results is generated and output (950). However, if it is determined that the training was insufficient, then no notification is generated or output. Alternatively, in certain embodiments, rather than providing no notification when the App determines that the training was insufficient, a notification indicating that training is not yet sufficient may be provided.

Figure 10:
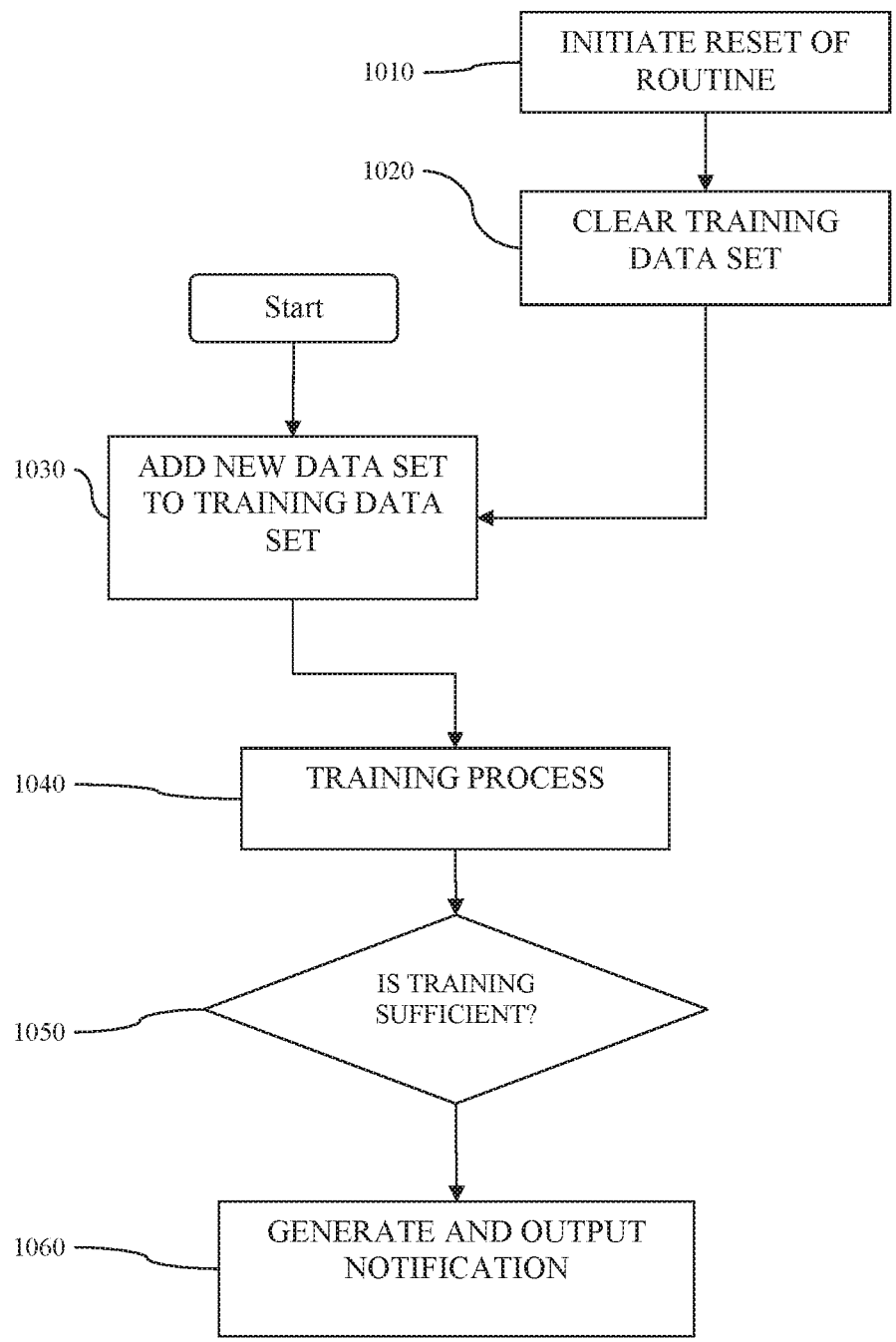
FIG. 10 illustrates a process flow for training and notification in accordance with another embodiment of the present disclosure.

FIG. 10 illustrates a process flow for training and notification in accordance with another embodiment of the present disclosure. As shown in FIG. 10, the data analysis training and notification routine is similar to the routine shown and described in FIG. 9, with the "forgetting" feature (920) replaced by a reset or clearing the training data set (1010 and 1020). Referring to FIG. 10, the initiating reset of routine (1010) and clearing the training data set (1020) in certain embodiments are implemented in response to actuation of an input button for example, on the user interface of the App to reset the training routine. In certain embodiments, the user initiates the reset of the routine (1010) and the training data set clears (1020) so as to update the learned correlation relationship between activity and future glucose levels by the App.

Referring to FIG. 10, when the reset is initiated, then the data training and notification routine is invoked periodically thereafter, and similar to the routine shown in FIG. 9, the new data set is added to the training data set (1030) and after the training process is complete (1040), it is determined whether the training is sufficient (1050). When it is determined that the training is sufficient, the App in certain embodiments generates and outputs notification to the user (1060). When it is determined that the training was insufficient (1060), then no notification is presented to the user, or alternatively, a notification indicating that the training was insufficient is generated by the App and presented to the user.

Within the scope of the present disclosure modifications to the data set training and notification routines described in conjunction with FIGS. 9 and 10 are contemplated where both the reset/clearing training data set (1010-1020, FIG. 10) feature and the "forgetting" feature (920, FIG. 9) are included in the same analysis routine. Also, in certain embodiments, the reset occurs periodically, such as once per year. Alternatively, in certain embodiments, the reset occur after the training has provided a valid notification (i.e., when it is determined that the training was sufficient).

In the manner described, in accordance with the embodiments of the present disclosure, Type-1 diabetic patients, Type-2 diabetic patients as well as pre-diabetics are provided with tools to monitor physiological conditions while engaged in daily routines and over time the App, for example, executable on a mobile phone of the user or the patient provides consistent glucose response to various types of activities and parameters that may impact the fluctuation in the user or the patient's glucose level. Such tools will allow the user or the patient to modify diet, exercise routine, or other daily activities knowing how the particular diet, exercise or activity affects the fluctuation in glucose level, and proactively take action to maintain the desired glycemic control and avoiding harmful glycemic excursions.

Embodiments of the present disclosure include aspects of data collection including detecting a particular activity and prompting the user or the patient to enter additional information related to the detected activity so as to render the data collection more robust. For example, using the activity monitor 130A, when the App executed on the mobile phone 110 detects continuous movement for a predetermined time period, the App, in certain embodiments, is configured to generate and output a query to the user interface 110A to prompt the user or the patient to either confirm that the detected activity is occurring, and/or add additional information related to the detected activity (which prompts, in certain embodiments, may be generated and output to the user interface 110A upon detection of the termination of the activity).

In this manner, in accordance with the embodiments of the present disclosure, robust physiological parameter monitoring system and dynamic glucose response pattern to provide consistent and reliable glucose response to physiological or other parameters and activities is provided.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method of determining a correlation between an overnight glucose level and an activity metric, comprising:

receiving, by a data analysis module, activity metric information and overnight glucose level information over a predetermined time period including a plurality of days;

categorizing, by the data analysis module, the overnight glucose level information for days within the predetermined time period with a significant activity metric into a first set, and the overnight glucose level information for days within the predetermined time period without the significant activity metric into a second set, wherein the first set comprises at least a plurality of days with a significant activity metric;

determining, by the data analysis module, a correlation between the overnight glucose level and the activity metric for each day of the first set;

fitting, by the data analysis module, the determined correlations to a predetermined function;

receiving, by the data analysis module, a measured level of activity metric for a second time period, the second time period including a single day;

determining, by the data analysis module, using the fitted predetermined function and the measured level of the activity metric for the second time period, an overnight glucose level for the second time period; and outputting, by the data analysis module, a therapy recommendation based on the determined overnight glucose level for the second time period on a user interface.

2. The method of claim 1, wherein the days within the predetermined time period with the significant activity metric includes a day with the activity metric exceeding a predetermined threshold, and further, wherein the days within the predetermined time period without the significant activity metric includes a day with the activity metric below the predetermined threshold.

3. The method of claim 2, wherein the activity metric includes an amount of calories burned during a 24 hour time period.

4. The method of claim 2, wherein the activity metric includes a number of steps recorded during a 24 hour time period.

5. The method of claim 2, wherein the activity metric includes one or more of a time duration of an activity, an intensity level of an activity, a location of the activity including altitude, a distance traveled during an activity, or a type of an activity.

6. The method of claim 1, wherein categorizing the overnight glucose level into the first set includes generating a plurality of first glucose metrics each associated with the overnight glucose level information for a corresponding one of the days with the significant activity metric, and categorizing the overnight glucose level into the second set includes generating a second glucose metric associated with the overnight glucose level information for all days without the significant activity metric.

7. The method of claim 6, wherein determining the correlation between the overnight glucose level for the first set and the activity metric includes modifying each of the plurality of the first glucose metrics with the generated second glucose metric to generate a corresponding modified plurality of first glucose metrics.

8. The method of claim 7, wherein determining the correlation includes identifying an association between each of the modified plurality of first glucose metrics with the activity metric for the corresponding day with the significant activity metric.

9. The method of claim 1, wherein receiving glucose level information includes generating signals corresponding to monitored glucose level with a glucose sensor.

10. The method of claim 9, wherein the glucose sensor generates the signals corresponding to the monitored glucose level from dermal fluid or interstitial fluid.

11. The method of claim 9, wherein the glucose sensor includes a plurality of electrodes including a working electrode comprising an analyte-responsive enzyme bonded to a polymer disposed on the working electrode.

12. The method of claim 11, wherein the analyte-responsive enzyme is chemically bonded to the polymer disposed on the working electrode.

13. The method of claim 11, wherein the working electrode comprises a mediator bonded to the polymer disposed on the working electrode.

14. The method of claim 13, wherein the mediator is crosslinked with the polymer disposed on the working electrode.

15. The method of claim 9, wherein the glucose sensor includes a plurality of electrodes including a working electrode comprising a mediator bonded to a polymer disposed on the working electrode.

16. The method of claim 1, wherein the outputted-therapy recommendation includes a recommendation to consume one or more of a medication, food, or drink.

17. The method of claim 1, wherein the predetermined function includes a linear function, a constant offset relationship, an exponential relationship, a logarithmic relationship, or a polynomial relationship.

18. An apparatus for determining a correlation between an overnight glucose level and an activity metric, comprising:
a data input interface for receiving glucose data over a predetermined time period including a plurality of days;
a data analysis module operatively coupled to the data input module, and configured to:
categorize the overnight glucose level information for days within the predetermined time period with a significant activity metric into a first set, and the overnight glucose level information for days within the predetermined time period without the significant activity metric into a second set, wherein the first set comprises at least a plurality of days with a significant activity metric;
determine a correlation between the overnight glucose level information and the activity metric for each day of the first set; and
fit the determined correlations to a predetermined function;
receive a measured level of activity metric for a second time period, the second time period including a single day;
determine, using the fitted predetermined function and the measured level of the activity metric for the second time period, an overnight glucose level for the second time period;
determine a therapy recommendation based on the determined overnight glucose level for the second time period; and
a data output interface operatively coupled to the data analysis module to output the therapy recommendation.

19. The apparatus of claim 18, wherein the days within the predetermined time period with the significant activity metric includes a day with the activity metric exceeding a predetermined threshold, and further, wherein the days within the predetermined time period without the significant activity metric includes a day with the activity metric below the predetermined threshold.

20. The apparatus of claim 19, wherein the activity metric includes an amount of calories burned during a 24 hour time period.

21. The apparatus of claim 19, wherein the activity metric includes a number of steps recorded during a 24 hour time period.

22. The apparatus of claim 19, wherein the activity metric includes one or more of a time duration of an activity, an intensity level of an activity, a location of the activity including altitude, a distance traveled during an activity, or a type of an activity.

23. The apparatus of claim 18, wherein the data analysis module configured to categorize the overnight glucose level into the first set generates a plurality of first glucose metrics each associated with the overnight glucose level information for a corresponding one of the days with the significant activity metric, and configured to categorize the overnight glucose level into the second set generates a second glucose metric associated with the overnight glucose level information for all days without the significant activity metric.

24. The apparatus of claim 23, wherein the data analysis module configured to determine the correlation between the overnight glucose level for the first set and the activity metric modifies each of the plurality of the first glucose metrics with the generated second glucose metric to generate a corresponding modified plurality of first glucose metrics.

25. The apparatus of claim 24, wherein the data analysis module configured to determine the correlation identifies an association between each of the modified plurality of first glucose metrics with the activity metric for the corresponding day with the significant activity metric.

26. The apparatus of claim 18, wherein the glucose level information is received from a glucose sensor positioned in fluid contact with bodily fluid to generate signals corresponding to the glucose data.

27. The apparatus of claim 26, wherein the bodily fluid includes dermal fluid or interstitial fluid.

28. The apparatus of claim 26, wherein the glucose sensor includes a plurality of electrodes including a working electrode comprising an analyte-responsive enzyme bonded to a polymer disposed on the working electrode.

29. The apparatus of claim 28, wherein the analyte-responsive enzyme is chemically bonded to the polymer disposed on the working electrode.

30. The apparatus of claim 28, wherein the working electrode comprises a mediator bonded to the polymer disposed on the working electrode.

31. The apparatus of claim 30, wherein the mediator is crosslinked with the polymer disposed on the working electrode.

32. The apparatus of claim 26, wherein the glucose sensor includes a plurality of electrodes including a working electrode comprising a mediator bonded to a polymer disposed on the working electrode.

33. The apparatus of claim 18, wherein the data output interface includes a user interface of one or more of a mobile telephone, a tablet computing device, a server, a laptop computer, or a wearable device including a smart watch.

34. The apparatus of claim 18, wherein the outputted therapy recommendation includes a recommendation to consume one or more of a medication, food, or drink.

35. The apparatus of claim 18, wherein the predetermined function includes a linear function, a constant offset relationship, an exponential relationship, a logarithmic relationship, or a polynomial relationship.

36. A method of determining a correlation between an overnight glucose level and an activity metric, comprising:
receiving, by a data analysis module, activity metric information and glucose level information over a predetermined time period including a plurality of days;
calculating, by the data analysis module, a relative change in glucose level information between day to night for the plurality of days in the predetermined time period;
categorizing, by the data analysis module, the relative change in glucose level information between day to night for days within the predetermined time period with a significant activity metric into a first set, and the relative change in glucose level information between day to night for days within the predetermined time period without the significant activity metric into a second set, wherein the first set comprises at least a plurality of days with a significant activity metric;
determining, by the data analysis module, a correlation between the relative change in glucose level information between day to night and the activity metric for each day of the first set;
fitting, by the data analysis module, the determined correlations to a predetermined function;
receiving, by the data analysis module, a measured level of activity metric for a second time period, the second time period including a single day;
determining, by the data analysis module, using the fitted predetermined function and the measured level of the activity metric for the second time period, an overnight glucose level for the second time period; and
outputting, by the data analysis module, a therapy recommendation based on the determined overnight glucose level for the second time period on a user interface.

37. The method of claim 36, wherein the days within the predetermined time period with the significant activity metric includes a day with the activity metric exceeding a predetermined threshold, and further, wherein the days within the predetermined time period without the significant activity metric includes a day with the activity metric below the predetermined threshold.

38. The method of claim 37, wherein the activity metric includes an amount of calories burned during a 24 hour time period.

39. The method of claim 37, wherein the activity metric includes a number of steps recorded during a 24 hour time period.

40. The method of claim 37, wherein the activity metric includes one or more of a time duration of an activity, an intensity level of an activity, a location of the activity including altitude, a distance traveled during an activity, or a type of an activity.

41. The method of claim 36, wherein categorizing the relative change in glucose level information between day to night into the first set includes generating a plurality of first glucose metrics each associated with the relative change in glucose level information between day to night for a corresponding one of the days with the significant activity metric, and categorizing the relative change in glucose level information between day to night into the second set includes generating a second glucose metric associated with the relative change in glucose level information between day to night for all days without the significant activity metric.

42. The method of claim 41, wherein determining the correlation between the relative change in glucose level information between day to night for the first set and the activity metric includes modifying each of the plurality of the first glucose metrics with the generated second glucose metric to generate a corresponding modified plurality of first glucose metrics.

43. The method of claim 42, wherein determining the correlation includes identifying an association between each of the modified plurality of first glucose metrics with the activity metric for the corresponding day with the significant activity metric.

44. The method of claim 36, wherein receiving glucose level information includes generating signals corresponding to monitored glucose level with a glucose sensor.

45. The method of claim 44, wherein the glucose sensor generates the signals corresponding to the monitored glucose level from dermal fluid or interstitial fluid.

46. The method of claim 44, wherein the glucose sensor includes a plurality of electrodes including a working electrode comprising an analyte-responsive enzyme bonded to a polymer disposed on the working electrode.

47. The method of claim 46, wherein the analyte-responsive enzyme is chemically bonded to the polymer disposed on the working electrode.

48. The method of claim 46, wherein the working electrode comprises a mediator bonded to the polymer disposed on the working electrode.

49. The method of claim 48, wherein the mediator is crosslinked with the polymer disposed on the working electrode.

50. The method of claim 44, wherein the glucose sensor includes a plurality of electrodes including a working electrode comprising a mediator bonded to a polymer disposed on the working electrode.

51. The method of claim 36, wherein the outputted therapy recommendation includes a recommendation to consume one or more of a medication, food, or drink.

52. The method of claim 36, wherein the predetermined function includes a linear function, a constant offset relationship, an exponential relationship, a logarithmic relationship, or a polynomial relationship.

53. An apparatus for determining a correlation between an overnight glucose level and an activity metric, comprising:
a data input interface for receiving glucose data over a predetermined time period including a plurality of days;
a data analysis module operatively coupled to the data input module, and configured to:
calculate a relative change in glucose level information between day to night for the plurality of days in the predetermined time period;
categorize the relative change in glucose level information between day to night for days within the predetermined time period with a significant activity metric into a first set and relative change in glucose level information between day to night for days within the predetermined time period without the significant activity metric into a second set wherein the first set comprises at least a plurality of days with a significant activity metric;
determine a correlation between relative change in glucose level information between day to night and the activity metric for each day of the first set; and
fit the determined correlations to a predetermined function;
receive a measured level of activity metric for a second time period, the second time period including a single day;
determine, using the fitted predetermined function and the measured level of the activity metric for the second time period, an overnight glucose level for the second time period;
determine a therapy recommendation based on the determined overnight glucose level for the second time period; and
a data output interface operatively coupled to the data analysis module to output the therapy recommendation.

54. The apparatus of claim 53, wherein the days within the predetermined time period with the significant activity metric includes a day with the activity metric exceeding a predetermined threshold, and further, wherein the days within the predetermined time period without the significant activity includes a day with the activity metric below the predetermined threshold.

55. The apparatus of claim 54, wherein the activity metric includes an amount of calories burned during a 24 hour time period.

56. The apparatus of claim 54, wherein the activity metric includes a number of steps recorded during a 24 hour time period.

57. The apparatus of claim 54, wherein the activity metric includes one or more of a time duration of an activity, an intensity level of an activity, a location of the activity including altitude, a distance traveled during an activity, or a type of an activity.

58. The apparatus of claim 53, wherein the data analysis module categorizing the first set generates a plurality of first glucose metrics each associated with the relative change in glucose level information between day to night for a corresponding one of the days with the significant activity metric, and generates a second glucose metric associated with the relative change in glucose level information between day to night for all days without the significant activity metric.

59. The apparatus of claim 58, wherein the data analysis module determining the correlation between the relative change in glucose level information between day to night for the first set and the activity metric modifies each of the plurality of the first glucose metrics with the generated second glucose metric to generate a corresponding modified plurality of first glucose metrics.

60. The apparatus of claim 59, wherein the data analysis module determining the correlation identifies an association between each of the modified plurality of first glucose metrics with the activity metric for the corresponding day with the significant activity metric.

61. The apparatus of claim 53, wherein the glucose level information is received from a glucose sensor positioned in fluid contact with bodily fluid to generate signals corresponding to the glucose level information.

62. The apparatus of claim 61, wherein the bodily fluid includes dermal fluid or interstitial fluid.

63. The apparatus of claim 61, wherein the glucose sensor includes a plurality of electrodes including a working electrode comprising an analyte-responsive enzyme bonded to a polymer disposed on the working electrode.

64. The apparatus of claim 63, wherein the analyte-responsive enzyme is chemically bonded to the polymer disposed on the working electrode.

65. The apparatus of claim 63, wherein the working electrode comprises a mediator bonded to the polymer disposed on the working electrode.

66. The apparatus of claim 65, wherein the mediator is crosslinked with the polymer disposed on the working electrode.

67. The apparatus of claim 61, wherein the glucose sensor includes a plurality of electrodes including a working electrode comprising a mediator bonded to a polymer disposed on the working electrode.

68. The apparatus of claim 53, wherein the data output interface includes a user interface of one or more of a mobile telephone, a tablet computing device, a server, a laptop computer, or a wearable device including a smart watch.

69. The apparatus of claim 53, wherein the outputted therapy recommendation includes a recommendation to consume one or more of a medication, food, or drink.

70. The apparatus of claim 53, wherein the predetermined function includes a linear function, a constant offset relationship, an exponential relationship, a logarithmic relationship, or a polynomial relationship.

\* \* \* \* \*